United States Patent
Gerber et al.

(10) Patent No.: US 10,994,064 B2
(45) Date of Patent: May 4, 2021

(54) PERITONEAL DIALYSATE FLOW PATH SENSING

(71) Applicant: Medtronic, Inc., Minneapolis, MN (US)

(72) Inventors: Martin T. Gerber, Maple Grove, MN (US); Christopher M. Hobot, Rogers, MN (US)

(73) Assignee: Medtronic, Inc., Minneapolis, MN (US)

( * ) Notice: Subject to any disclaimer, the term of this patent is extended or adjusted under 35 U.S.C. 154(b) by 317 days.

(21) Appl. No.: 15/666,614

(22) Filed: Aug. 2, 2017

(65) Prior Publication Data
US 2018/0043075 A1 Feb. 15, 2018

Related U.S. Application Data

(60) Provisional application No. 62/373,133, filed on Aug. 10, 2016.

(51) Int. Cl.
*A61M 1/28* (2006.01)
*A61M 1/16* (2006.01)

(52) U.S. Cl.
CPC .......... *A61M 1/28* (2013.01); *A61M 1/1609* (2014.02); *A61M 1/1619* (2014.02);
(Continued)

(58) Field of Classification Search
CPC .............. A61M 1/28; A61M 2205/702; A61M 2205/52; A61M 2205/502;
(Continued)

(56) References Cited

U.S. PATENT DOCUMENTS

| 3,602,222 A | 8/1971 | Herndon |
| 3,608,729 A | 9/1971 | Haselden |

(Continued)

FOREIGN PATENT DOCUMENTS

| CN | 1273535 | 11/2000 |
| CN | 1643368 A | 7/2005 |

(Continued)

OTHER PUBLICATIONS

PCTUS20170146199 ISR and written opinion, dated Feb. 19, 2018.

(Continued)

*Primary Examiner* — Amber R Stiles

(57) ABSTRACT

The invention relates to systems and methods for sensing fluid characteristics of peritoneal dialysate infused into and removed from a patient during treatment. The systems and methods include sensors, processors, and flow paths for determining patient health based on the fluid characteristics of the peritoneal dialysate. The system can be a peritoneal dialysis cycler which can include an infusion line; an effluent line; at least one pump positioned in the infusion and/or effluent line; and at least one sensor fluidly connected to the effluent line. The sensor can be at least one of a flow sensor, an ion selective electrode, a pH sensor, a pressure sensor, a refractive index sensor, and a temperature sensor. The method can include infusing peritoneal dialysate through an infusion line; removing peritoneal dialysate through an effluent line; and determining at least one fluid characteristic of the peritoneal dialysate in the effluent line.

21 Claims, 2 Drawing Sheets

(52) U.S. Cl.
CPC ... *A61M 1/1696* (2013.01); *A61M 2205/3317* (2013.01); *A61M 2205/3324* (2013.01); *A61M 2205/3327* (2013.01); *A61M 2205/3331* (2013.01); *A61M 2205/3337* (2013.01); *A61M 2205/3368* (2013.01); *A61M 2205/50* (2013.01); *A61M 2205/502* (2013.01); *A61M 2205/52* (2013.01); *A61M 2205/702* (2013.01)

(58) Field of Classification Search
CPC ...... A61M 2205/50; A61M 2205/3368; A61M 2205/3337; A61M 2205/3331; A61M 2205/3324; A61M 2205/3317; A61M 2205/3327; A61M 1/1696; A61M 1/1619; A61M 1/1609; G01N 11/00
See application file for complete search history.

(56) References Cited

U.S. PATENT DOCUMENTS

| | | | |
|---|---|---|---|
| 3,669,878 | A | 6/1972 | Marantz |
| 3,669,880 | A | 6/1972 | Marantz |
| 3,730,183 | A | 5/1973 | Goldsmith |
| 3,754,867 | A | 8/1973 | Guenther |
| 3,850,835 | A | 11/1974 | Marantz |
| 3,884,808 | A | 5/1975 | Scott |
| 3,989,622 | A | 11/1976 | Marantz |
| 3,989,625 | A | 11/1976 | Mason |
| 4,060,485 | A | 11/1977 | Eaton |
| 4,371,385 | A | 2/1983 | Johnson |
| 4,374,382 | A | 2/1983 | Markowitz |
| 4,381,999 | A | 5/1983 | Boucher |
| 4,460,555 | A | 7/1984 | Thompson |
| 4,556,063 | A | 12/1985 | Thompson |
| 4,562,751 | A | 1/1986 | Nason |
| 4,581,141 | A | 4/1986 | Ash |
| 4,650,587 | A | 3/1987 | Polak |
| 4,661,246 | A | 4/1987 | Ash |
| 4,678,408 | A | 7/1987 | Mason |
| 4,685,903 | A | 8/1987 | Cable |
| 4,747,822 | A | 5/1988 | Peabody |
| 4,750,494 | A | 6/1988 | King |
| 4,772,560 | A | 9/1988 | Attar |
| 4,799,493 | A | 1/1989 | DuFault |
| 4,826,663 | A | 5/1989 | Alberti |
| 4,828,693 | A | 5/1989 | Lindsay |
| 4,976,683 | A | 12/1990 | Gauthier |
| 5,032,265 | A | 7/1991 | Jha |
| 5,080,653 | A | 1/1992 | Voss |
| 5,091,642 | A | 2/1992 | Chow |
| 5,092,886 | A | 3/1992 | Dobos-Hardy |
| 5,097,122 | A | 3/1992 | Colman |
| 5,127,404 | A | 7/1992 | Wyborny |
| 5,141,493 | A * | 8/1992 | Jacobsen ............ A61M 1/1696 210/104 |
| 5,247,434 | A * | 9/1993 | Peterson ................ A61M 1/16 210/646 |
| 5,284,470 | A | 2/1994 | Beltz |
| 5,302,288 | A | 4/1994 | Meidl |
| 5,305,745 | A | 4/1994 | Zacouto |
| 5,318,750 | A | 6/1994 | Lascombes |
| 5,468,388 | A | 11/1995 | Goddard |
| 5,507,723 | A | 4/1996 | Keshaviah |
| 5,643,201 | A | 7/1997 | Peabody |
| 5,651,893 | A | 7/1997 | Kenley |
| 5,683,432 | A | 11/1997 | Goedeke |
| 5,685,988 | A * | 11/1997 | Malchesky ......... A61M 1/1696 210/195.2 |
| 5,744,031 | A | 4/1998 | Bene |
| 5,762,782 | A | 6/1998 | Kenley |
| 5,819,007 | A | 10/1998 | Elghazzawi |
| 5,902,336 | A | 5/1999 | Mishkin |
| 5,944,684 | A | 8/1999 | Roberts |
| 5,987,352 | A | 11/1999 | Klein |
| 6,048,732 | A | 4/2000 | Anslyn |
| 6,052,622 | A | 4/2000 | Holmstrom |
| 6,058,331 | A | 5/2000 | King |
| 6,156,002 | A | 12/2000 | Polaschegg |
| 6,230,059 | B1 | 5/2001 | Duffin |
| 6,248,093 | B1 | 6/2001 | Moberg |
| 6,254,567 | B1 | 7/2001 | Treu |
| 6,321,101 | B1 | 11/2001 | Holmstrom |
| 6,362,591 | B1 | 3/2002 | Moberg |
| 6,363,279 | B1 | 3/2002 | Ben-Haim |
| 6,505,075 | B1 | 1/2003 | Weiner |
| 6,554,798 | B1 | 4/2003 | Mann |
| 6,555,986 | B2 | 4/2003 | Moberg |
| 6,589,229 | B1 | 7/2003 | Connelly |
| 6,602,399 | B1 | 8/2003 | Fromherz |
| 6,609,023 | B1 | 8/2003 | Fischell |
| 6,627,164 | B1 | 9/2003 | Wong |
| 6,645,191 | B1 | 11/2003 | Knerr |
| 6,676,608 | B1 | 1/2004 | Keren |
| 6,689,083 | B1 | 2/2004 | Gelfand |
| 6,706,007 | B2 | 3/2004 | Gelfand |
| 6,711,439 | B1 | 3/2004 | Bradley |
| 6,726,647 | B1 | 4/2004 | Sternby |
| 6,780,322 | B1 | 8/2004 | Bissler |
| 6,818,196 | B2 | 11/2004 | Wong |
| 6,878,283 | B2 | 4/2005 | Thompson |
| 6,887,214 | B1 | 5/2005 | Levin |
| 6,890,315 | B1 | 5/2005 | Levin |
| 6,960,179 | B2 | 11/2005 | Gura |
| 7,074,332 | B2 | 7/2006 | Summerton |
| 7,077,819 | B1 | 7/2006 | Goldau |
| 7,131,956 | B1 | 11/2006 | Pirazzoli |
| 7,175,809 | B2 | 2/2007 | Gelfand |
| 7,207,946 | B2 | 4/2007 | Sirokman |
| 7,208,092 | B2 | 4/2007 | Micheli |
| 7,276,042 | B2 | 10/2007 | Polaschegg |
| 7,399,289 | B2 | 7/2008 | Gelfand |
| 7,404,799 | B1 | 7/2008 | Koh |
| 7,500,958 | B2 | 3/2009 | Asbrink |
| 7,566,432 | B2 | 7/2009 | Wong |
| 7,575,564 | B2 | 8/2009 | Childers |
| 7,610,086 | B1 | 10/2009 | Ke |
| 7,674,231 | B2 | 3/2010 | McCombie |
| 7,704,361 | B2 | 4/2010 | Garde |
| 7,736,507 | B2 | 6/2010 | Wong |
| 7,744,553 | B2 | 6/2010 | Kelly |
| 7,754,852 | B2 | 7/2010 | Burnett |
| 7,756,572 | B1 | 7/2010 | Fard |
| 7,775,983 | B2 | 8/2010 | Zhang |
| 7,775,986 | B2 | 8/2010 | Roeher |
| 7,776,210 | B2 | 8/2010 | Rosenbaum |
| 7,785,463 | B2 | 8/2010 | Bissler |
| 7,794,141 | B2 | 9/2010 | Perry |
| 7,850,635 | B2 | 12/2010 | Polaschegg |
| 7,857,976 | B2 | 12/2010 | Bissler |
| 7,867,214 | B2 | 1/2011 | Childers |
| 7,896,831 | B2 | 3/2011 | Sternby |
| 7,922,686 | B2 | 4/2011 | Childers |
| 7,922,911 | B2 | 4/2011 | Micheli |
| 7,947,179 | B2 | 5/2011 | Rosenbaum |
| 7,955,291 | B2 | 6/2011 | Sternby |
| 7,967,022 | B2 | 6/2011 | Grant |
| 7,981,082 | B2 | 7/2011 | Wang |
| 8,000,000 | B2 | 8/2011 | Greenberg |
| 8,034,161 | B2 | 10/2011 | Gura |
| 8,070,709 | B2 | 12/2011 | Childers |
| 8,096,969 | B2 | 1/2012 | Roberts |
| 8,105,260 | B2 | 1/2012 | Tonelli |
| 8,183,046 | B2 | 5/2012 | Lu |
| 8,187,250 | B2 | 5/2012 | Roberts |
| 8,197,439 | B2 | 6/2012 | Wang |
| 8,202,241 | B2 | 6/2012 | Karakama |
| 8,246,826 | B2 | 8/2012 | Wilt |
| 8,273,049 | B2 | 9/2012 | Demers |
| 8,282,828 | B2 | 10/2012 | Wallenas |
| 8,292,594 | B2 | 10/2012 | Tracey |
| 8,313,642 | B2 | 11/2012 | Yu |
| 8,317,492 | B2 | 11/2012 | Demers |
| 8,357,113 | B2 | 1/2013 | Childers |
| 8,366,316 | B2 | 2/2013 | Kamen |

(56) References Cited

U.S. PATENT DOCUMENTS

| | | |
|---|---|---|
| 8,366,655 B2 | 2/2013 | Kamen |
| 8,404,091 B2 | 3/2013 | Ding |
| 8,409,441 B2 | 4/2013 | Wilt |
| 8,496,809 B2 | 7/2013 | Roger |
| 8,499,780 B2 | 8/2013 | Wilt |
| 8,500,676 B2 | 8/2013 | Jansson |
| 8,512,271 B2 | 8/2013 | Moissl |
| 8,518,260 B2 | 8/2013 | Raimann |
| 8,521,482 B2 | 8/2013 | Akonur |
| 8,535,525 B2 | 9/2013 | Heyes |
| 8,560,510 B2 | 10/2013 | Brueggerhoff |
| 8,580,112 B2 | 11/2013 | Updyke |
| 8,597,227 B2 | 12/2013 | Childers |
| 8,696,626 B2 | 4/2014 | Kirsch |
| 8,903,492 B2 | 12/2014 | Soykan |
| 8,926,542 B2 | 1/2015 | Gerber |
| 9,907,897 B2 | 3/2018 | Burbank |
| 10,046,100 B2 | 8/2018 | Burbank |
| 2002/0016550 A1 | 2/2002 | Sweeney |
| 2002/0042561 A1 | 4/2002 | Schulman |
| 2002/0107474 A1 * | 8/2002 | Noack ............... A61M 1/28 604/29 |
| 2002/0112609 A1 | 8/2002 | Wong |
| 2003/0028089 A1 | 2/2003 | Galley |
| 2003/0069481 A1 | 4/2003 | Hervy |
| 2003/0080059 A1 | 5/2003 | Peterson |
| 2003/0097086 A1 | 5/2003 | Gura |
| 2003/0105435 A1 | 6/2003 | Taylor |
| 2003/0113931 A1 | 6/2003 | Pan |
| 2003/0114787 A1 | 6/2003 | Gura |
| 2003/0187479 A1 | 10/2003 | TranThong |
| 2004/0019312 A1 | 1/2004 | Childers |
| 2004/0060865 A1 | 4/2004 | Callan |
| 2004/0068219 A1 | 4/2004 | Summerton |
| 2004/0099593 A1 | 5/2004 | DePaolis |
| 2004/0147900 A1 | 7/2004 | Polaschegg |
| 2004/0168969 A1 | 9/2004 | Sternby |
| 2004/0215090 A1 | 10/2004 | Erkkila |
| 2005/0065760 A1 | 3/2005 | Murtfeldt |
| 2005/0113796 A1 | 5/2005 | Taylor |
| 2005/0126961 A1 | 6/2005 | Bissler |
| 2005/0131331 A1 | 6/2005 | Kelly |
| 2005/0126998 A1 | 7/2005 | Childers |
| 2005/0150832 A1 | 7/2005 | Tsukamoto |
| 2005/0214863 A1 | 9/2005 | McDevitt |
| 2005/0234354 A1 | 10/2005 | Rowlandson |
| 2005/0234357 A1 | 10/2005 | Xue |
| 2005/0234381 A1 | 10/2005 | Niemetz |
| 2005/0234534 A1 | 10/2005 | Rowlandson |
| 2005/0236330 A1 | 10/2005 | Nier |
| 2005/0265895 A1 | 12/2005 | Kopelman |
| 2005/0274658 A1 | 12/2005 | Rosenbaum |
| 2006/0025661 A1 | 2/2006 | Sweeney |
| 2006/0025748 A1 | 2/2006 | Ye |
| 2006/0217771 A1 | 2/2006 | Soykan |
| 2006/0058731 A1 | 3/2006 | Burnett |
| 2006/0191850 A1 | 8/2006 | Bosetto |
| 2006/0195064 A1 | 8/2006 | Plahey |
| 2006/0226079 A1 | 10/2006 | Mori |
| 2006/0241709 A1 | 10/2006 | Soykan |
| 2006/0247548 A1 | 11/2006 | Sarkar |
| 2006/0264894 A1 | 11/2006 | Moberg |
| 2007/0007208 A1 | 1/2007 | Brugger |
| 2007/0038138 A1 | 2/2007 | Gill |
| 2007/0066928 A1 | 3/2007 | Lannoy |
| 2007/0073168 A1 | 3/2007 | Zhang |
| 2007/0138011 A1 | 6/2007 | Hofmann |
| 2007/0161113 A1 | 7/2007 | Ash |
| 2007/0175827 A1 | 8/2007 | Wariar |
| 2007/0179431 A1 | 8/2007 | Roberts |
| 2007/0213653 A1 | 9/2007 | Childers |
| 2007/0215545 A1 | 9/2007 | Bissler |
| 2007/0255250 A1 | 11/2007 | Moberg |
| 2007/0276270 A1 | 11/2007 | Tran |
| 2008/0006570 A1 | 1/2008 | Gura |
| 2008/0021337 A1 | 1/2008 | Li |
| 2008/0053905 A9 | 3/2008 | Brugger |
| 2008/0067132 A1 | 3/2008 | Ross |
| 2008/0093276 A1 | 4/2008 | Roger |
| 2008/0200866 A1 | 8/2008 | Prisco |
| 2008/0215247 A1 | 9/2008 | Tonelli |
| 2008/0253427 A1 | 10/2008 | Kamen |
| 2009/0020471 A1 | 1/2009 | Tsukamoto |
| 2009/0101577 A1 | 4/2009 | Fulkerson |
| 2009/0124869 A1 | 5/2009 | Hu |
| 2009/0124963 A1 | 5/2009 | Hogard |
| 2009/0127193 A1 | 5/2009 | Updyke |
| 2009/0149776 A1 | 6/2009 | Adams |
| 2009/0171261 A1 | 7/2009 | Sternby |
| 2009/0264776 A1 | 10/2009 | Vardy |
| 2009/0275849 A1 | 11/2009 | Stewart |
| 2009/0275883 A1 | 11/2009 | Chapman |
| 2009/0281484 A1 | 11/2009 | Childers |
| 2009/0282980 A1 | 11/2009 | Gura |
| 2009/0299272 A1 * | 12/2009 | Hopping ............... A61M 1/28 604/29 |
| 2009/0314063 A1 | 12/2009 | Sternby |
| 2010/0004588 A1 | 1/2010 | Yeh |
| 2010/0010425 A1 | 1/2010 | Yu |
| 2010/0010429 A1 | 1/2010 | Childers |
| 2010/0042035 A1 | 2/2010 | Moissl |
| 2010/0076398 A1 | 3/2010 | Scheurer |
| 2010/0078381 A1 | 4/2010 | Merchant |
| 2010/0078387 A1 | 4/2010 | Wong |
| 2010/0084330 A1 | 4/2010 | Wong |
| 2010/0087771 A1 | 4/2010 | Karakama |
| 2010/0094158 A1 | 4/2010 | Solem |
| 2010/0113891 A1 | 5/2010 | Barrett |
| 2010/0114012 A1 | 5/2010 | Sandford |
| 2010/0137693 A1 | 6/2010 | Porras |
| 2010/0137782 A1 | 6/2010 | Jansson |
| 2010/0168546 A1 | 7/2010 | Kamath |
| 2010/0217180 A1 | 8/2010 | Akonur |
| 2010/0217181 A1 | 8/2010 | Roberts |
| 2010/0224492 A1 | 9/2010 | Ding |
| 2010/0234795 A1 | 9/2010 | Wallenas |
| 2010/0241045 A1 | 9/2010 | Kelly |
| 2010/0264086 A1 | 10/2010 | Noack |
| 2010/0312172 A1 | 12/2010 | Hoffman |
| 2011/0017665 A1 | 1/2011 | Updyke |
| 2011/0048949 A1 | 3/2011 | Ding et al. |
| 2011/0066006 A1 | 3/2011 | Banet |
| 2011/0066043 A1 | 3/2011 | Banet |
| 2011/0071465 A1 | 3/2011 | Wang |
| 2011/0077574 A1 | 3/2011 | Sigg |
| 2011/0077575 A1 | 3/2011 | Kraemer |
| 2011/0079558 A1 | 4/2011 | Raimann |
| 2011/0081728 A1 | 4/2011 | Putnam |
| 2011/0087187 A1 | 4/2011 | Beck |
| 2011/0100909 A1 | 5/2011 | Stange |
| 2011/0106003 A1 | 5/2011 | Childers |
| 2011/0130666 A1 | 6/2011 | Dong |
| 2011/0137136 A1 | 6/2011 | Kotanko |
| 2011/0141116 A1 | 6/2011 | Dalesch |
| 2011/0144570 A1 | 6/2011 | Childers |
| 2011/0184340 A1 | 7/2011 | Tan |
| 2011/0208105 A1 | 8/2011 | Brandl |
| 2011/0272337 A1 | 11/2011 | Palmer |
| 2011/0301447 A1 | 12/2011 | Park |
| 2011/0301472 A1 | 12/2011 | Grober |
| 2012/0016228 A1 | 1/2012 | Kroh |
| 2012/0029937 A1 | 2/2012 | Neftel |
| 2012/0083729 A1 | 4/2012 | Childers |
| 2012/0085707 A1 | 4/2012 | Beiriger |
| 2012/0115248 A1 | 5/2012 | Ansyln |
| 2012/0135396 A1 | 5/2012 | McDevitt |
| 2012/0181230 A1 | 7/2012 | Kloeffel |
| 2012/0220528 A1 | 8/2012 | VanAntwerp |
| 2012/0258545 A1 | 10/2012 | Ash |
| 2012/0258546 A1 | 10/2012 | Marran |
| 2012/0259276 A1 | 10/2012 | Childers |
| 2012/0273354 A1 * | 11/2012 | Orhan ............... A61M 1/284 204/519 |
| 2012/0273415 A1 | 11/2012 | Gerber |

(56) References Cited

U.S. PATENT DOCUMENTS

| | | |
|---|---|---|
| 2012/0273420 A1 | 11/2012 | Gerber |
| 2012/0277546 A1 | 11/2012 | Soykan |
| 2012/0277551 A1 | 11/2012 | Gerber |
| 2012/0277552 A1 | 11/2012 | Gerber |
| 2012/0277604 A1 | 11/2012 | Gerber |
| 2012/0277650 A1 | 11/2012 | Gerber |
| 2012/0277655 A1 | 11/2012 | Gerber |
| 2012/0277722 A1 | 11/2012 | Gerber |
| 2012/0283581 A1 | 11/2012 | Olde et al. |
| 2012/0303079 A1 | 11/2012 | Mahajan |
| 2013/0037465 A1 | 2/2013 | Heyes |
| 2013/0062265 A1 | 3/2013 | Balschat |
| 2013/0116578 A1 | 5/2013 | QiAn |
| 2013/0168316 A1 | 7/2013 | Noguchi |
| 2013/0186759 A1 | 7/2013 | Lin |
| 2013/0193073 A1 | 8/2013 | Hogard |
| 2013/0199998 A1 | 8/2013 | Kelly |
| 2013/0211730 A1 | 8/2013 | Wolff |
| 2013/0213890 A1 | 8/2013 | Kelly |
| 2013/0228517 A1 | 9/2013 | Roger |
| 2013/0231607 A1 | 9/2013 | Roger |
| 2013/0248426 A1 | 9/2013 | Pouchoulin |
| 2013/0274642 A1 | 10/2013 | Soykan |
| 2013/0324915 A1 | 12/2013 | (Krensky)Britton |
| 2013/0330208 A1 | 12/2013 | Ly |
| 2013/0331774 A1 | 12/2013 | Farrell |
| 2014/0018727 A1 * | 1/2014 | Burbank ............ A61M 1/1656 604/28 |
| 2014/0018728 A1 | 1/2014 | Plahey |
| 2014/0042092 A1 | 2/2014 | Akonur |
| 2014/0065950 A1 | 3/2014 | Mendelsohn |
| 2014/0088442 A1 | 3/2014 | Soykan |
| 2014/0110340 A1 | 4/2014 | White |
| 2014/0110341 A1 | 4/2014 | White |
| 2014/0158538 A1 | 6/2014 | Collier |
| 2014/0158623 A1 | 6/2014 | Pudil |
| 2014/0190876 A1 | 7/2014 | Meyer |
| 2014/0216250 A1 | 8/2014 | Meyer |
| 2014/0217028 A1 | 8/2014 | Pudil |
| 2014/0217029 A1 | 8/2014 | Meyer |
| 2014/0217030 A1 | 8/2014 | Meyer |
| 2014/0220699 A1 | 8/2014 | Pudil |
| 2014/0314625 A1 | 10/2014 | Clift |
| 2015/0032023 A1 | 1/2015 | Soykan |
| 2015/0080682 A1 | 3/2015 | Gerber |
| 2015/0088047 A1 | 3/2015 | Gerber |
| 2015/0144539 A1 | 5/2015 | Pudil |
| 2015/0148697 A1 | 5/2015 | Burnes |
| 2015/0149096 A1 | 5/2015 | Soykan |
| 2015/0250427 A1 | 9/2015 | Soykan |
| 2015/0343126 A1 | 12/2015 | Merchant |
| 2015/0352269 A1 | 12/2015 | Gerber |
| 2015/0367054 A1 | 12/2015 | Gerber |
| 2016/0023467 A1 | 2/2016 | Smith |
| 2016/0143774 A1 | 5/2016 | Burnett |
| 2016/0206801 A1 | 7/2016 | Gerber |
| 2016/0331884 A1 | 11/2016 | Sigg |
| 2018/0043080 A1 | 2/2018 | Gerber |

FOREIGN PATENT DOCUMENTS

| | | |
|---|---|---|
| CN | 101193667 | 6/2008 |
| CN | 101300476 A | 11/2008 |
| CN | 202048893 | 3/2011 |
| CN | 103037917 | 4/2013 |
| CN | 103619372 | 3/2014 |
| CN | 103717132 | 9/2014 |
| CN | 104833635 A | 8/2015 |
| CN | 104884102 | 9/2015 |
| CN | 105008893 B | 10/2015 |
| DE | 3224823 | 1/1984 |
| EP | 0266795 A2 | 11/1987 |
| EP | 0402505 | 12/1990 |
| EP | 0272414 | 10/1991 |
| EP | 1124599 | 5/2000 |
| EP | 1175238 | 11/2000 |
| EP | 1085295 | 11/2001 |
| EP | 1281351 | 2/2003 |
| EP | 2308526 | 10/2003 |
| EP | 1364666 A1 | 11/2003 |
| EP | 1523347 | 1/2004 |
| EP | 1523350 | 1/2004 |
| EP | 0906768 B1 | 2/2004 |
| EP | 1691863 | 4/2005 |
| EP | 2116269 | 2/2008 |
| EP | 1450879 | 10/2008 |
| EP | 1514562 | 4/2009 |
| EP | 2219703 | 5/2009 |
| EP | 1592494 B1 | 6/2009 |
| EP | 2100553 A1 | 9/2009 |
| EP | 2398529 | 11/2010 |
| EP | 2575827 A2 | 12/2010 |
| EP | 2100553 | 8/2011 |
| EP | 2576453 A2 | 12/2011 |
| EP | 2701580 | 11/2012 |
| EP | 2701595 | 11/2012 |
| EP | 1345856 B1 | 3/2013 |
| EP | 2344220 B1 | 4/2013 |
| EP | 1351756 | 7/2013 |
| EP | 2190498 | 7/2013 |
| EP | 2701596 | 3/2014 |
| EP | 1582226 | 1/2016 |
| JP | S55138462 | 10/1980 |
| JP | S63-143077 | 11/1987 |
| JP | 2002533170 | 10/2002 |
| JP | 2002542900 | 12/2002 |
| JP | 2003235965 | 8/2003 |
| JP | 2005-533573 | 11/2005 |
| JP | 5-99464 | 10/2012 |
| JP | 5099464 | 10/2012 |
| WO | 1995003839 | 2/1995 |
| WO | WO 1998054563 | 12/1998 |
| WO | WO-9906082 A1 * | 2/1999 ............ A61M 1/28 |
| WO | WO1999006082 | 2/1999 |
| WO | 9937342 | 7/1999 |
| WO | 0057935 | 10/2000 |
| WO | WO2000057935 A1 | 10/2000 |
| WO | 200066197 A1 | 11/2000 |
| WO | 200170307 A1 | 9/2001 |
| WO | 2001085295 A2 | 9/2001 |
| WO | 0185295 A2 | 11/2001 |
| WO | 2002013691 | 2/2002 |
| WO | WO 20020053211 | 7/2002 |
| WO | 2003043677 A2 | 5/2003 |
| WO | 2003043680 | 5/2003 |
| WO | 2003051422 A2 | 6/2003 |
| WO | 2004008826 | 1/2004 |
| WO | 2004009156 | 1/2004 |
| WO | 2004009158 | 1/2004 |
| WO | 2004030716 A2 | 4/2004 |
| WO | 2004030717 A2 | 4/2004 |
| WO | 2004064616 A2 | 8/2004 |
| WO | 2005033701 | 4/2005 |
| WO | 2005061026 | 7/2005 |
| WO | 2005123230 A2 | 12/2005 |
| WO | 2006011009 | 2/2006 |
| WO | 2006017446 | 2/2006 |
| WO | 2007038347 | 4/2007 |
| WO | 2007089855 A2 | 8/2007 |
| WO | WO2009094035 A1 | 1/2008 |
| WO | 2008037410 | 4/2008 |
| WO | 2009026603 | 12/2008 |
| WO | 2009024566 | 2/2009 |
| WO | 2009026603 A1 | 3/2009 |
| WO | 2009061608 | 5/2009 |
| WO | 2009094184 | 7/2009 |
| WO | 2009157877 A1 | 12/2009 |
| WO | 2009157878 A1 | 12/2009 |
| WO | WO2009154955 A2 | 12/2009 |
| WO | 2010024963 | 3/2010 |
| WO | 2010028860 | 3/2010 |
| WO | 2010028860 A1 | 3/2010 |
| WO | 2010033314 | 3/2010 |

(56) References Cited

FOREIGN PATENT DOCUMENTS

| WO | 2010033699 | 3/2010 |
|---|---|---|
| WO | 2010077851 | 7/2010 |
| WO | WO 20100002830 | 7/2010 |
| WO | 2010096659 | 10/2010 |
| WO | 2010121820 | 10/2010 |
| WO | 2011025705 A1 | 3/2011 |
| WO | 2011026645 | 3/2011 |
| WO | WO2013022760 A1 | 8/2011 |
| WO | WO 2011/132046 | 10/2011 |
| WO | 2011137693 | 11/2011 |
| WO | WO2011161056 | 12/2011 |
| WO | 2012042323 | 4/2012 |
| WO | 2012050781 | 4/2012 |
| WO | 2012051996 | 4/2012 |
| WO | 2012073420 | 7/2012 |
| WO | WO 2012/129501 | 9/2012 |
| WO | 2012148781 | 11/2012 |
| WO | 2012148784 | 11/2012 |
| WO | 2012148786 | 11/2012 |
| WO | 2012148787 A1 | 11/2012 |
| WO | 2012148789 | 11/2012 |
| WO | 2012162515 A2 | 11/2012 |
| WO | WO2012148788 A1 | 11/2012 |
| WO | WO 20120148784 | 11/2012 |
| WO | 2012172398 | 12/2012 |
| WO | 2013019179 A1 | 2/2013 |
| WO | 2013019994 A2 | 2/2013 |
| WO | 2013025844 | 2/2013 |
| WO | 2013028809 A3 | 2/2013 |
| WO | 2013101292 | 7/2013 |
| WO | 2013103607 A1 | 7/2013 |
| WO | 2013103906 | 7/2013 |
| WO | 2013110906 | 8/2013 |
| WO | 2013110919 | 8/2013 |
| WO | 2013114063 A1 | 8/2013 |
| WO | 2013121162 A1 | 8/2013 |
| WO | 2013140346 | 9/2013 |
| WO | 2013141896 | 9/2013 |
| WO | 2013101292 A3 | 10/2013 |
| WO | 14066254 | 5/2014 |
| WO | 14066255 | 5/2014 |
| WO | 14077082 | 5/2014 |
| WO | 2014121162 | 8/2014 |
| WO | 2014121163 | 8/2014 |
| WO | 2014121167 | 8/2014 |
| WO | 2014121169 | 8/2014 |
| WO | WO2014121161 | 8/2014 |
| WO | WO 20140121169 | 8/2014 |
| WO | WO2015081221 A1 | 6/2015 |
| WO | WO 20150130205 | 9/2015 |
| WO | WO 20150159280 | 10/2015 |
| WO | WO2016049542 | 3/2016 |
| WO | WO 20160080883 | 5/2016 |
| WO | WO 20170034452 | 3/2017 |
| WO | WO 2017/176687 | 10/2017 |
| WO | WO 2017/176701 | 10/2017 |

OTHER PUBLICATIONS

PCTUS2017025858 International Search Report dated Jun. 29, 2017.
PCTUS2017025858 Written Opinion dated Jun. 29, 2017.
PCT/US2017/025868 International Search Report dated Jun. 29, 2017.
PCT/US2017/025868 Written Opinion dated Jun. 29, 2017.
PCTUS2017025876 International Search Report dated Jun. 29, 2017.
PCTUS2017025876 Written Opinion dated Jun. 29, 2017.
European Search Report for App. No. 17185636.2, dated Mar. 27, 2018.
European Search Report for App. No. 17185636.2 dated Jan. 10, 2018.
European Search Report for App. No. 17185808.7, dated Jan. 2, 2018.
European Search Report for App. No. 17185638.8, dated Dec. 19, 2017.
Chinese Office Action for App. No. 201710669451.8, dated Sep. 12, 2019.
PCT/US2017/030377 International Search Report dated Sep. 1, 2017.
PCT/US2017/030377 Written Opinion dated Sep. 1, 2017.
[NPL121] Roberts M, The regenerative dialysis (REDY) sorbent system. Nephrology, 1998, 275-278:4.
[NPL138] U.S. Appl. No. 61/480,544, dated Apr. 29, 2011.
[NPL149] PCT/US/2012/034329, International Search Report, dated Dec. 3, 2012.
[NPL15] PCT International Search Report from International Application No. PCT/US2014/067650, dated Mar. 9, 2015.
[NPL170] Bleyer, et al, Kidney International. Jun. 2006; 69(12):2268-2273.
[NPL188] PCT/US2012/034333, International Search Report, dated Aug. 29, 2012.
[NPL238] PCT Application, PCT/US2013/020404, filed Jan. 4, 2013.
[NPL23] U.S. Appl. No. 13/424,525, published Nov. 1, 2012.
[NPL285] Zoccali, Pulmonary Congestion Predicts Cardiac Events and Mortality in ESRD, Clinical Epidemiology, J. Am Soc Nephrol 24:639-646, 2013.
[NPL310] U.S. Appl. No. 61/480,532, filed Apr. 29, 2011.
[NPL311] U.S. Appl. No. 13/424,479, published Nov. 1, 2012.
[NPL313] U.S. Appl. No. 13/424,525, published Nov. 1, 2013.
[NPL317] U.S. Appl. No. 61/480,530, filed Apr. 29, 2011.
[NPL47] U.S. Appl. No. 61/480,544. unpublished.
[NPL495] European Office Action in Application 12717020.7 dated Sep. 14, 2016.
[NPL55] U.S. Appl. No. 13/424,454, dated Nov. 1, 2012.
[NPL57] U.S. Appl. No. 13/424,467, published Nov. 1, 2012.
[NPL62] U.S. Appl. No. 13/424,533, dated Nov. 1, 2012.
[NPL67] U.S. Appl. No. 13/424,490, published Nov. 1, 2012.
[NPL68] U.S. Appl. No. 13/424,517, dated Nov. 1, 2012.
[NPL699] Office Action in Chinese Application No. 201280020937.4 dated Mar. 22, 2016.
[NPL] Green et al., Sudden Cardiac Death in Hemodialysis Patients: an In-Depth Review , Am J Kidney Dis 57(6)921:929; published Apr. 18, 2011.
[NPL] Rajan et al. Generalized Feature Extraction for Time-Varying Autoregressive Models, IEEE Transacion Signal Processing vol. 44, No. 10; published Oct. 1, 1996.
Chinese Office Action in App. No. 201710669452.2, dated May 11, 2020.
European Search Report for App. No. 17190066.5, dated Jan. 16, 2018.
European Search Report for App. No. 17190084.8, dated Feb. 9, 2018.
European search report for App. No. 19219612.9, dated Apr. 29, 2020.
Chinese Office Action for App. No. 201710669454.1, dated Jul. 3, 2020.
European Office Action for App. No. 17754582.9, dated Aug. 10, 2020.
European Search Report for App. No. 17185810.3, dated Dec. 15, 2017.
Office Action in Chinese App. No. 201710778666.3 dated Sep. 19, 2019.
International Preliminary Report on Patentability for App. No. PCT/US2019/019334, dated Jun. 12, 2019.
Indian OA dated Nov. 21, 2019 in 2981/KOLNP/2013.
Chinese Office Action for App. No. 2019071601874110, dated Jul. 19, 2019.
Henderson, et al, "Online Preparation of Sterile Pyrogen-Free Electrolyte Solution," Trans. Am. Soc. Artif.Intern.Organs, 1978 pp. 465-467.
[NPL757] U.S. Appl. No. 60/650,497 dated Feb. 7, 2005.
[NPL81] U.S. Appl. No. 61/480,539 dated Apr. 29, 2011.
[NPL90] Nedelkov, et. al., Design of buffer exchange surfaces and sensor chips for biosensor chip mass spectrometry, Proteomics, 2002, 441-446, 2(4).

(56) References Cited

OTHER PUBLICATIONS

[NPL] European Search Report App 14865374.4, dated Jun. 12, 2017.
[NPL] European Search Report for Application No. 14865128.4 dated Jun. 20, 2017.
Castellanos, et al, Clinical Relevance of Intraperitoneal Pressure in Peritoneal Dialysis Patients, Perit Dial Int. Sep.-Oct. 2017;37(5):562-567. doi: 10.3747/pdi.2016.00267. Epub Jul. 11, 2017.
Chinese Office Action in App. No. 201480059332.5, dated Mar. 30, 2018.
Dejardin, et al, Intraperitoneal pressure in PD patients: relationship to intraperitoneal volume, body size and PD-related complications, Nephrol Dial Transplant. May 2007;22(5):1437-44.
European Search Report for App. No. 14859115.9, dated Jan. 5, 2018.
[NPL582] Office Action in U.S. Appl. No. 13/757,792 dated Apr. 6, 2015.
[NPL633] Gordhandas et al, Real-Time Extraction and Analysis of Key Morphological Features in the Electrocardiogram, for Data Compression and Clinical Decision Support, 2004, Computational Physiology, pp. 15-18.
[NPL674] Office Action in Chinese Application No. 201280020932.1 dated Jan. 7, 2015.
[NPL727] Office Action in European Application No. EP 12717021.5 dated Feb. 3, 2017.
[NPL84] U.S. Appl. No. 61/480,535 dated Apr. 29, 2011.
[NPL501] Office Action in U.S. Appl. No. 13/424,467 dated Oct. 16, 2013.
[NPL547] Office Action in Chinese Application No. 201510511657.9 dated Dec. 28, 2016.
European Search Report for App. No. 17190053.3, dated Jan. 2, 2018.
PCT/US2016/058579 International Search Report dated Jan. 31, 2017.
Wollenstein, et al, "Colorimetric gas sensors for the detection of ammonia, nitrogen dioxide, and carbon monoxide: current status and research trends", Sensor and Test Conference 2011, Jan. 2, 2011, pp. 562-567.
Written Opinion in Dutch App. No. 2018577, dated Nov. 2, 2017.
European Search Report for App. No. 17190066, dated Jan. 16, 2018.
Laurent, Jeanpierre, "Continuous Monitoring of Dynamic Systems: Application to Monitoring of Dialyzed Patients" Oct. 30, 2004, received from Internet: http://laurent.jeanpierre1.free.fr/recherche/papiers/aista2004.pdf.
[NPL105] Brynda, et. al., The detection of toman 2-microglobuiin by grating coupler immunosensor with three dimensional antibody networks. Biosensors & Bioelectronics, 1999, 363-368, 14(4).
[NPL10] Wheaton, et al., Dowex Ion Exchange Resins-Fundamentals of Ion Exchange; Jun. 2000, pp. 1-9. http://www.dow.com/scripts/litorder.asp?filepath=liquidseps/pdfs/noreg/177-01837.pdf.
[NPL111] Zhong, et. al., Miniature urea sensor based on H(+)-ion sensitive field effect transistor and its application in clinical analysis, Chin. J. Biotechnol., 1992, 57-65. 8(1).
[NPL119] PCT/US2012/034331, International Search Report and Written Opinion dated Jul. 9, 2012.
[NPL139] U.S. Appl. No. 61/480,541 dated Apr. 29, 2011.
[NPL142] Hemametrics, Crit-Line Hematocrit Accuracy, 2003, 1-5, vol. 1, Tech Note No. 11 (Rev. D).
[NPL146] PCT/US2012/034334, International Search Report, dated Jul. 6, 2012.
[NPL147] PCT/US2012/034335, International Search Report, dated Sep. 5, 2012.
[NPL148] PCT/US/2012/034327, International Search Report, dated Aug. 13, 2013.
[NPL14] Foley, et al., Long Interdialytic Interval and Martality among Patients Receiving Hemodialysis, N Engl Jrnl Med. 2011:365(12):1099-1107.

[NPL15] PCT International Search Report from International Application No. PCT/US2014/067650, dated Nov. 27, 2013.
[NPL169] Wang, Fundamentals of intrathoracic impedance monitoring in heart failure, Am. J. Cardiology, 2007, 3G-10G: Suppl.
[NPL16] PCT/US2014/067650 International Search Report Written Opinion dated Mar. 9, 2015.
[NPL180] PCT/US2012/034335, International Preliminary Report on Patentability, dated Nov. 7, 2013.
[NPL186] PCT/US2012/034332, Internatonal Preliminary Report on Patentability, dated Oct. 29, 2013.
[NPL188] PCT/US2012/034333, International Search Report, dated Aug. 29, 2013.
[NPL197] PCT/US2012/034330, International Preliminary Report on Patentability, dated Oct. 29, 2013.
[NPL205] Culleton, BF et al. Effect of Frequent Nocturnal Hemodialysis vs. Conventional Hemodialysis on Left Ventricular Mass and Quality of Life. 2007 Journal of the American Medical Association 298 (11), 1291-1299.
[NPL219] U.S. Appl. No. 13/791,755, filed Mar. 8, 2013.
[NPL220] U.S. Appl. No. 13/757,792, filed Feb. 2, 2013.
[NPL222] U.S. Appl. No. 13/757,794, filed Feb. 2, 2013.
[NPL227] U.S. Appl. No. 13/837,287, filed Mar. 15, 2013.
[NPL22] U.S. Appl. No. 13/424,429 dated Nov. 1, 2012.
[NPL230] Redfield, et. al, Restoration of renal response to atrial natriuretic factor in experimental low-output heat failure, Am. J. Physiol., Oct. 1, 1989, R917-923:257.
[NPL231] Rogoza, et. al., Validation of A&D UA-767 device for the self-measurement of blood pressure, Blood Pressure Monitoring, 2000, 227-231, 5(4).
[NPL233] PCT/US2012/034329, International Preliminary Report on Patentability, dated Oct. 29, 2013.
[NPL234] Lima, et. al., An electrochemical sensor based on nanostructure hollsndite-type manganese oxide for detection of potassium ion, Sensors, Aug. 24, 2009, 6613-8625, 9.
[NPL235] Maclean, et, al., Effects of hindlimb contraction on pressor and muscle interstitial metabolite responses in the cat, J. App. Physiol., 1998, 1583-1592, 85(4).
[NPL237] U.S. Appl. No. 13/757,693, dated Feb. 1, 2013.
[NPL240] U.S. Appl. No. 13/836,973, filed Mar. 15, 2013.
[NPL241] U.S. Appl. No. 14/259,655, filed Apr. 23, 2014.
[NPL242] U.S. Appl. No. 14/259,589, filed Apr. 23, 2014.
[NPL264] PCT/US2014/014357 International Search Report and Written Opinion dated May 19, 2014.
[NPL268] Ronco et al. 2008, Cardiorenal Syndrome, Journal American College Cardiology, 52:1527-1539, Abstract.
[NPL26] Overgaard, et. al., Activity-induced recovery of excitability in K+-depressed rat soleus muscle, Am. J. P 280: R48-R55, Jan. 1, 2001.
[NPL27] Overgaard. et. al., Relations between excitability and contractility in rate soleusmuscle: role of the NA+-K+ pump and NA+-K-S gradients. Journal of Physiology, 1999, 215-225, 518(1).
[NPL306] Coast, et al. 1990, An approach to Cardiac Arrhythmia analysis Using Hidden Markov Models, IEEE Transactions on Biomedical Engineering. 1990, 37(9):826-835.
[NPL309] Weiner, et. al., Article: Cardiac Function and Cardiovascular Disease in Chronic Kidney Disease, Book: Primer on Kidney Diseases (Author: Greenberg, et al), 2009,499-505, 5th Ed., Saunders Elsevier, Philadelphia, PA.
[NPL312] U.S. Appl. No. 13/424,429 dated Nov. 1, 2012.
[NPL318] U.S. Appl. No. 61/480,528 dated Apr. 29, 2011.
[NPL323] Whitman, CKD and Sudden Cardiac Death: Epidemiology, Mechanisms, and Therapeutic Approaches, J Am Soc Nephrol, 23:1929-1939, 2012.
[NPL324] Hall, Hospitalization for Congestive Heart Failure: United States, 2000-2010, NCHS Data Brief, No. 108, Oct. 2012.
[NPL325] Albert, Fluid Management Strategies in Heart Failure, Critical Care Nurse, 32:20-32, 2012.
[NPL326] PCT/US2014/065201 International Search Report dated May 26, 2015.
[NPL328] Genovesi, et al., Nephrology, Dialysis, Transplantation 2009; 24(8):2529-2536.

(56) References Cited

OTHER PUBLICATIONS

[NPL32] Secemsky, et. al, High prevalence of cardiac autonomic dysfunction and T-wave alternans in dialysis patients. Heart Rhythm, Apr. 2011, 592-598 : vol. 8, No. 4.
[NPL339] U.S. Appl. No. 13/424,517 IDS, filed Aug. 2, 2012.
[NPL340] U.S. Appl. No. 13/424,517, IDS filed Dec. 2, 2013.
[NPL35] Wei, et. al., Fullerene-cryptand coated piezoelectric crystal urea sensor based on urease, Analytica Chimica Acta, 2001,77-85:437.
[NPL376] Gambro AK 96 Dialysis Machine Operators Manual, Dec. 2012. p. 1-140.
[NPL376] Gambro AK 96 Dialysis Machine Operators Manual, Dec. 2012. p. 421-534.
[NPL37] U.S. Appl. No. 13/368,225 dated Feb. 7, 2012.
[NPL384] Talaia, Terminal Velocity of a Bubble Rise in a Liquid Column, World Acad. of Sci., Engineering & Tech., vol. 28, pp. 264-268, Published Jan. 1, 2007.
[NPL386] The FHN Trial Group. In-Center. Hemodialysis Six Times per Week versus Three Times per Week, New England Journal of Medicine, 2010 Abstract.
[NPL39] PCT/US2012/034332, International Search Report, dated Jul. 5, 2012.
[NPL46] Siegenthaler, et al., Pulmonary fluid status monitoring with intrathoracic impedance, Journal of Clinical Monitoring and Computing, 24:449-451, published Jan. 12, 2011.
[NPL477] Office Action in U.S. Appl. No. 13/757,792 dated Apr. 6, 2015.
[NPL483] Office Action in U.S. Appl. No. 13/424,525 dated Aug. 11, 2015.
[NPL486] Office Action in U.S. Appl. No. 13/424,525 dated Oct. 20, 2016.
[NPL494] John Wm Agar: Review: Understanding sorbent dialysis systems, Nephrology, vol. 15, No. 4, Jun. 1, 2010, pp. 406-411.
[NPL500] Office Action in U.S. Appl. No. 14/554,272 dated Aug. 8, 2016.
[NPL503] Office Action in U.S. Appl. No. 13/424,490 dated Oct. 22, 2013.
[NPL504] Office Action in U.S. Appl. No. 13/424,490 dated Mar. 10, 2014.
[NPL505] Office Action in U.S. Appl. No. 13/424,490 dated Jul. 14, 2014.
[NPL506] Office Action in U.S. Appl. No. 13/424,490 dated Dec. 5, 2014.
[NPL507] Office Action in U.S. Appl. No. 13/424,525 dated Sep. 29, 2014.
[NPL508] Office Action in U.S. Appl. No. 13/424,525 dated May 6, 2015.
[NPL509] Office Action in U.S. Appl. No. 13/424,454 dated Oct. 17, 2013.
[NPL510] Office Action in U.S. Appl. No. 13/424,454 dated Mar. 10, 2014.
[NPL511] Office action in U.S. Appl. No. 13/424,429 dated Oct. 15, 2015.
[NPL512] Office Action in U.S. Appl. No. 12/571,127 dated Feb. 27, 2014.
[NPL513] Office Action in U.S. Appl. No. 12/571,127 dated Jul. 6, 2015.
[NPL514] Office Action in U.S. Appl. No. 12/571,127 dated Dec. 17, 2015.
[NPL521] Office Action in U.S. Appl. No. 14/554,338 dated Jun. 7, 2016.
[NPL522] Office Action in U.S. Appl. No. 14/554,338 dated Sep. 28, 2016.
[NPL524] Office Action in U.S. Appl. No. 13/424,429 dated Oct. 15, 2015.
[NPL525] Office Action in U.S. Appl. No. 12/571,127 dated Feb. 27, 2014.
[NPL526] Office Action in U.S. Appl. No. 12/571,127 dated Jul. 6, 2015.
[NPL527] Office Action in U.S. Appl. No. 12/571,127 dated Dec. 17, 2015.
[NPL539] Office Action in U.S. Appl. No. 12/571,127 dated Nov. 8, 2012.
[NPL540] Office Action in U.S. Appl. No. 14/554,338 dated Jun. 7, 2016.
[NPL541] Office Action in U.S. Appl. No. 14/554,338 dated Sep. 28, 2016.
[NPL542] Office Action in U.S. Appl. No. 14/554,272 dated Aug. 8, 2016.
[NPL543] Office Action in U.S. Appl. No. 13/424,479 dated Oct. 25, 2014.
[NPL545] Office Action in U.S. Appl. No. 14/566,686 dated Apr. 28, 2016.
[NPL502] Office Action in U.S. Appl. No. 13/424,467 dated Mar. 3, 2014.
[NPL632] Lakerveld et al, Primary prevention of diabetes mellitus type 2 and cardiovascular diseases using a cognitive behavior program aimed at lifestyle changes in people at risk: Design of a randomized controlled trial, 2008, BMC Endocrine Disorders, 8(6): 1-19.
[NPL671] European Office Action in Application 12717020.7 dated Dec. 11, 2015.
[NPL672] PCT/US2012/034331 International Preliminary Report on Patentability and Written Opinion dated Oct. 29, 2013.
[NPL675] Office Action in Chinese Application No. 201280020932.1 dated Apr. 3, 2015.
[NPL693] PCT/US2012/034330, International Search Report and Written Opinion dated Aug. 28, 2012.
[NPL699] Office Action in Chinese Application No. 201280020937.4 dated Oct. 22, 2016.
[NPL700] Office Action in Japanese Application No. 2014-508434 dated Nov. 16, 2015.
[NPL701] Office Action in Japanese Application No. 2014-508434 dated Dec. 8, 2014.
[NPL702] Office Action in Japanese Application No. 2014-508434 dated Nov. 4, 2016.
[NPL703] Office Action in European Application No. 12717019.9 dated Feb. 16, 2017.
[NPL706] Office Action in Chinese Application No. 201510511657.9 dated May 10, 2017.
[NPL709] PCT/US2014/065201 International Preliminary Report on Patentability dated May 19, 2016.
[NPL735] Office Action in Chinese Application No. 201510593695.3 dated Jul. 12, 2017.
[NPL748] Office Action in European Application No. EP 12719170.8 dated Jan. 14, 2015.
[NPL749] Office Action in Japanese Application No. JP 2014-508437 dated Dec. 8, 2014.
Chinese OA in 201710669452.2 dated Oct. 16, 2019.
Chinese Office Action for App. No. 201710669452.2, dated Dec. 3, 2019.
European Search Report for App. No. 20198933.2, dated Dec. 22, 2020.

* cited by examiner

PERITONEAL DIALYSATE FLOW PATH SENSING

CROSS-REFERENCE TO RELATED APPLICATIONS

This application claims the benefit of and priority to U.S. Provisional Patent Application No. 62/373,133 filed Aug. 10, 2016, the entire disclosure of which is incorporated by reference herein.

FIELD OF THE INVENTION

The invention relates to systems and methods for sensing fluid characteristics of peritoneal dialysate infused into and removed from a patient during treatment. The systems and methods include sensors, processors, and flow paths for determining patient health based on the fluid characteristics of the peritoneal dialysate.

BACKGROUND

Peritoneal Dialysis (PD) is a dialysis treatment that differs from Hemodialysis (HD) because blood is not removed from the body and passed through a dialyzer, but a catheter is placed in the peritoneal cavity and dialysate removed and introduced directly into the peritoneal cavity. Blood is cleaned inside the patient using the patient's own peritoneum as a type of dialysis membrane. The two primary classes of PD are Continuous Ambulatory Peritoneal Dialysis (CAPD) and Continuous Cycling Peritoneal Dialysis (CCPD) (or Automated Peritoneal Dialysis (APD)). In CAPD, dialysis is performed continuously by positioning a bag of peritoneal dialysate at shoulder level and using gravity to pull the fluid into the peritoneal cavity. The used dialysate is then drained from the cavity and discarded. The time period that the dialysate is in the cavity is called the dwell time and can range from 30 minutes to 4 hours or more. CAPD is typically performed three, four or five times in a 24-hour period while a patient is awake. CAPD requires no cycler to deliver and remove the fluid.

Determination of specific fluid characteristics of the peritoneal dialysate infused into and removed from the patient allows for optimization of treatment and early medical intervention in the event of worsening health. Known systems do not provide adequate mechanisms to determine fluid characteristics of the dialysate used in peritoneal dialysis during treatment. In particular, known systems do not allow the effluent or filtrate removed from the patient to be sensed.

Hence, there is a need for systems and methods for determining fluid characteristics of the peritoneal dialysate. The need extends to systems and methods monitoring the fluid characteristics during treatment. There is also a need for systems and methods to remove portions of the peritoneal dialysate over the course of treatment to determine any changes to the peritoneal dialysate while in the peritoneal cavity of the patient.

SUMMARY OF THE INVENTION

The first aspect of the invention relates to a peritoneal dialysis cycler. In any embodiment, the peritoneal dialysis cycler can include a combined infusion and effluent line for delivering and receiving a peritoneal dialysate to and from a peritoneal cavity; at least one pump positioned in the combined infusion and effluent line; and at least one sensor fluidly connected to the combined infusion and effluent line, wherein the at least one sensor is selected from the group of: a flow sensor, an ion selective electrode, a pH sensor, a pressure sensor, a refractive index sensor, and a temperature sensor. In any embodiment, the combined infusion and effluent line can be separated into two different lines, which can be referred to as an infusion line and an effluent line.

In any embodiment, the peritoneal dialysis cycler can include a sampling flow path fluidly connected to the combined infusion and effluent line, wherein the at least one sensor is positioned in the sampling flow path; a valve connecting the combined infusion and effluent line to the sampling flow path; and at least one pump in the sampling flow path.

In any embodiment, the peritoneal dialysis cycler can include a detachable sampling reservoir fluidly connected to the sampling flow path.

In any embodiment, the peritoneal dialysis cycler can include a peritoneal dialysate generation flow path fluidly connected to the combined infusion and effluent line; the peritoneal dialysate generation flow path having a water source; a water purification module; at least one concentrate source fluidly connected to the peritoneal dialysate generation flow path; and at least one sensor positioned in the peritoneal dialysate generation flow path or infusion line. If two separate infusion and effluent lines are used, the peritoneal dialysate generation flow path can be fluidly connected to the infusion line.

In any embodiment, the peritoneal dialysis cycler can include a dialysate regeneration module; the dialysate regeneration module fluidly connected to the combined infusion and effluent line and the peritoneal dialysate generation flow path. If two separate infusion and effluent lines are used, the dialysate regeneration module can be fluidly connected to the effluent line.

In any embodiment, the dialysate regeneration module can be positioned downstream of the sampling flow path.

In any embodiment, the peritoneal dialysis cycler can include a processor in communication with the at least one sensor; the processor receiving data from the sensor and storing the data in a machine-readable storage medium.

In any embodiment, the processor can include an input/output interface, the input/output interface providing data from the at least one sensor to a user.

In any embodiment, the peritoneal dialysis cycler can include a sampling port fluidly connected to the combined infusion and effluent line. If two separate infusion and effluent lines are used, the sampling port fluidly connected can be fluidly connected to the effluent line.

In any embodiment, the sampling port can be covered by a pierceable septum.

The features disclosed as being part of the first aspect of the invention can be in the first aspect of the invention, either alone or in combination.

The second aspect of the invention is drawn a method. In any embodiment, the method can include the steps of infusing peritoneal dialysate into a patient through a combined infusion and effluent line; and determining at least one fluid characteristic of the peritoneal dialysate in the effluent line. In any embodiment, the method can include the steps of infusing peritoneal dialysate into a patient through a separate infusion line; removing peritoneal dialysate from the patient through a separate effluent line In any embodiment, the method can include the step of pumping the peritoneal dialysate from the effluent line to a sampling reservoir; wherein the step of determining at least one fluid characteristic of the peritoneal dialysate includes determining the fluid characteristic in the peritoneal dialysate in the sampling reservoir.

In any embodiment, the method can include the step of adding one or more reagents to the peritoneal dialysate in the sampling reservoir prior to determining the fluid characteristic.

In any embodiment, the method can include the step of removing a portion of fluid from the combined infusion and effluent line through a sampling port, wherein the step of determining at least one fluid characteristic of the peritoneal dialysate includes determining the fluid characteristic in the removed fluid. If two separate infusion and effluent lines are used, the step of removing a portion of fluid can be performed using the effluent line.

In any embodiment, the method can include the step of determining at least one fluid characteristic in the peritoneal dialysate in the combined infusion and effluent line. If two separate infusion and effluent lines are used, the step of determining at least one fluid characteristic in the peritoneal dialysate can be performed using the infusion line.

In any embodiment, at least one fluid characteristic can be determined in any one of the combined infusion and effluent line, the infusion line, and the effluent line.

In any embodiment, the fluid characteristic can be selected from the group of a pH of the fluid, and a volume of the fluid.

In any embodiment, the method can include the steps of a portion of the peritoneal dialysate from the patient through the effluent line at a first time; removing a portion of the peritoneal dialysate from the patient through the effluent at a second time; and determining the fluid characteristic at the first time and the second time.

In any embodiment, the fluid characteristic can be selected from the group of pH and concentration of one or more solutes.

In any embodiment, the method can include the step of communicating the fluid characteristic to a machine-readable storage medium in a processor.

The features disclosed as being part of the second aspect of the invention can be in the second aspect of the invention, either alone or in combination.

DETAILED DESCRIPTION OF THE INVENTION

Figure 1:
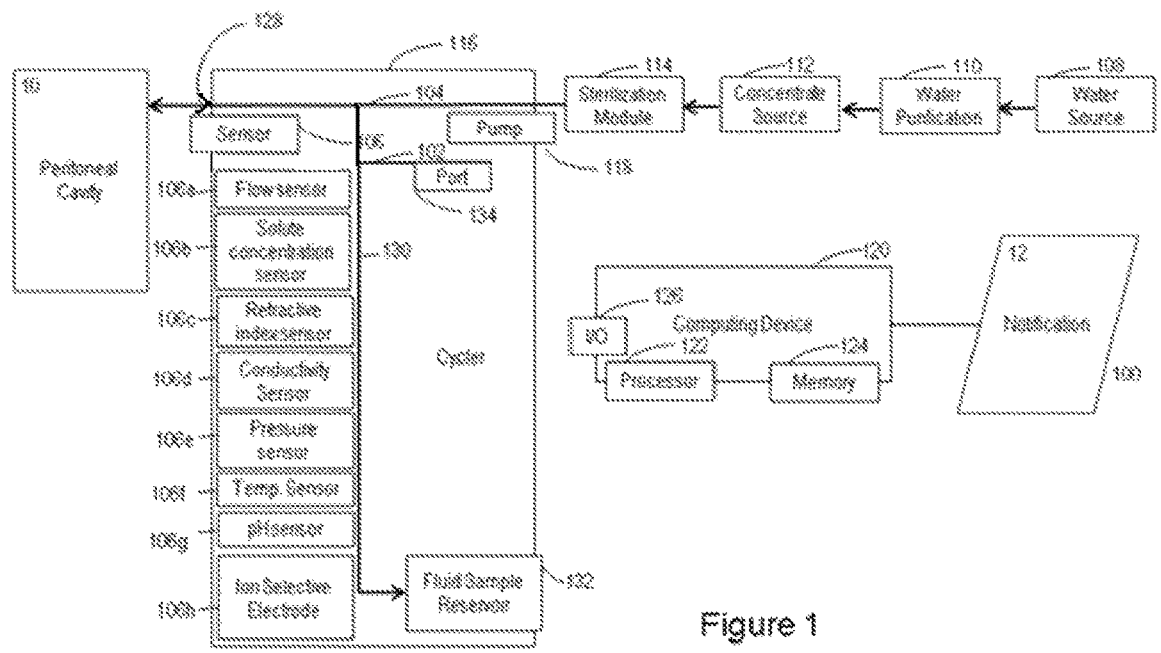
FIG. 1 is a schematic of a system for sensing fluid characteristics of peritoneal dialysate in a flow path.

Unless defined otherwise, all technical and scientific terms used generally have the same meaning as commonly understood by one of ordinary skill in the art.

The articles "a" and "an" are used to refer to one or to over one (i.e., to at least one) of the grammatical object of the article. For example, "an element" means one element or over one element.

The term "combined infusion and effluent line" refers to a fluid connector for delivering and removing fluid from a peritoneal cavity of a patient. The combined infusion and effluent line can optionally be separated into an independent infusion line and an independent effluent line.

The terms "communication" and "communicating" refer to an electronic or wireless link between two components.

The term "comprising" includes, but is not limited to, whatever follows the word "comprising." Use of the term indicates the listed elements are required or mandatory but that other elements are optional and can be present.

A "concentrate source" is a source of one or more solutes. The concentrate source can have one or more solutes with a solute concentration greater than the solute concentration to be used for dialysis. The concentrate in the concentrate source can also be lower than the solute concentration generally used in dialysis for generation of low concentration dialysate.

The terms "concentration" and "solute concentration" refers to an amount of a solute dissolved in a given amount of a solvent.

The term "conductivity sensor" refers to any component capable of measuring the electrical conductance or the electrical resistance of a fluid.

The term "consisting of" includes and is limited to whatever follows the phrase "consisting of" The phrase indicates the limited elements are required or mandatory and that no other elements can be present.

The term "consisting essentially of" includes whatever follows the term "consisting essentially of" and additional elements, structures, acts or features that do not affect the basic operation of the apparatus, structure or method.

The term "detachable" relates to any component of that can be separated from a system, module, cartridge or any component of the invention. "Detachable" can also refer to a component that can be taken out of a larger system with minimal time or effort. In certain instances, the components can be detached with minimal time or effort, but in other instances can require additional effort. The detached component can be optionally reattached to the system, module, cartridge or other component.

The terms "determining" and "determine" refer to ascertaining a particular state of a system or variable(s).

The term "dialysate regeneration module" refers to a component or components capable of removing waste products from a fluid.

The term "downstream" refers to a position of a first component in a flow path relative to a second component wherein fluid will pass by the second component prior to the first component during normal operation. The first component can be said to be "downstream" of the second component, while the second component is "upstream" of the first component.

The term "effluent line" refers to a fluid connector for removing fluid from a peritoneal cavity of a patient. The term "effluent line" can also refer to a combined effluent and infusion line.

The term "flow sensor" refers to any component capable of measuring a volume or a rate of fluid moving through a conduit.

A "fluid" is a liquid substance optionally having a combination of gas and liquid phases in the fluid. Notably, a liquid can therefore also have a mixture of gas and liquid phases of matter.

A "fluid characteristic" is any sensed characteristic of a fluid, including temperature, pressure, concentration, color, or any other characteristic.

The terms "fluidly connectable," "fluidly connected," "fluid connection" "fluidly connectable," or "fluidly connected" refer to the ability to pass fluid, gas, or mixtures thereof from one point to another point. The two points can be within or between any one or more of compartments, modules, systems, and components, all of any type.

The term "infusing" or to "infuse" a fluid refers to the movement of peritoneal dialysate into the peritoneal cavity of a patient.

An "infusion line" is a fluid line for carrying peritoneal dialysate into a body cavity or part of a patient such as a peritoneal cavity. The term "infusion line" can also refer to a combined effluent and infusion line.

The term "input/output interface" refers to a module of a processor or computing system that allows data to be received by the processor or computing system and provided by the processor or computing system. The input/output interfaces can automatically receive and provide data from sensors, or can receive data manually input through the interface, such as by a keyboard.

An "integrated cycler" is a component for movement of fluid into and out of the peritoneal cavity of a patient, wherein the integrated cycler forms a part of an overall system. For example, the integrated cycler can be contained in a housing with other components used for peritoneal dialysis and be in fluid and electrical connection with desired components.

The term "ion selective electrode" refers to any component capable of determining a concentration of a specific ion in a fluid based on a detected electrical potential.

The term "machine-readable storage medium" refers to any electronic device capable of storing information in a digital format for reading by a computer, processor, or other electronic device.

A "patient" or "subject" is a member of any animal species, preferably a mammalian species, optionally a human. The subject can be an apparently healthy individual, an individual suffering from a disease, or an individual being treated for a disease.

"Peritoneal dialysate" is a dialysis solution to be used in peritoneal dialysis having specified parameters for purity and sterility. Peritoneal dialysate is different than a dialysate used in hemodialysis, although peritoneal dialysate can be used in hemodialysis.

A "peritoneal dialysate generation flow path" is a path used in generating dialysate suitable for peritoneal dialysis.

"Peritoneal dialysis" is a therapy wherein a dialysate is infused into the peritoneal cavity, which serves as a natural dialyzer. In general, waste components diffuse from a patient's bloodstream across a peritoneal membrane into the dialysis solution via a concentration gradient. In general, excess fluid in the form of plasma water flows from a patient's bloodstream across a peritoneal membrane into the dialysis solution via an osmotic gradient. Once the infused peritoneal dialysis solution has captured sufficient amounts of the waste components the fluid is removed. The cycle can be repeated for several cycles each day or as needed.

The term "peritoneal dialysis cycler" or "cycler" refers to components for movement of fluid into and out of the peritoneal cavity of a patient, with or without additional components for generating peritoneal dialysate or performing additional functions.

The term "pH" refers to the hydrogen ion concentration in a fluid.

The term "pH sensor" refers to any component capable of measuring the hydrogen ion concentration in a fluid.

The term "pierceable septum" refers to a component through which a needle or syringe can be inserted to draw fluid out of a flow path.

The term "portion of fluid" refers to an amount of a fluid less than the entire amount of the fluid in a flow path, container, or reservoir.

The term "positioned" refers to the location of a component.

The term "pressure sensor" refers to any component capable of determining the force exerted by a fluid.

The term "processor" is a broad term and is to be given its ordinary and customary meaning to a person of ordinary skill in the art. The term refers without limitation to a computer system, state machine, and/or processor designed to perform arithmetic or logic operations using logic circuitry that responds to and processes the basic instructions that drive a computer. In any embodiment of the first, second, third, and fourth invention, the terms can include ROM ("read-only memory") and/or RAM ("random-access memory") associated therewith.

The term "pump" refers to any device that causes the movement of fluids or gases by applying suction or pressure.

The terms "pumping," "pumped," or to "pump" refers to moving or flowing a fluid using a pump of any type known to those of ordinary skill in the art.

The term "reagent" refers to a substance that will react with a second substance to produce an observable change in a solution.

The term "receiving" or to "receive" means to obtain information from any source.

A "refractive index sensor" is any component capable of detecting the ratio of the speed of light through a fluid to the speed of light through water. The concentration of one or more solutes in the fluid can be determined based on the refractive index.

The term "removing" fluid refers to flowing fluid out of a container, system, or patient.

The term "sampling flow path" refers to a flow path diverted from a main flow path in which fluid characteristics of a fluid in the sampling flow path can be determined.

The term "sampling port" refers to a fluid port in a flow path through which a portion of the fluid in the flow path can be removed for analysis.

The term "sampling reservoir" refers to a container for collecting a portion of a fluid for analysis of the fluid separate from the rest of a system.

A "sensor" is a component capable of determining one or more states of one or more variables in a system.

A "solute" is a substance dissolved in, or intended to be dissolved in, a solvent.

The term "storing" or to "store" refers to saving electronic data or information in a machine readable medium.

A "temperature sensor" is any component capable of measuring the temperature of a fluid.

The term "transmitting" or to "transmit" refers to sending information electronically.

A "valve" is a device capable of directing the flow of fluid or gas by opening, closing or obstructing one or more pathways to allow the fluid or gas to travel in a path. One or more valves configured to accomplish a desired flow can be configured into a "valve assembly."

The term "volume" refers to an amount of a fluid.

The term "water purification module" refers to a component or components capable of removing biological or chemical contaminants from water.

The term "water source" refers to a source from which potable water can be obtained.

Peritoneal Dialysis Fluid Path Sensing

FIG. 1 illustrates a system 100 for sampling peritoneal dialysate removed from a peritoneal cavity 10 of a patient.

The system 100 can include a combined peritoneal dialysate effluent line and infusion line 128, referred to herein as an effluent line, a peritoneal dialysate generation flow path 104, at least one sensor 106-106*h*, a peritoneal dialysis cycler 116, and a computing device 120. The effluent line 128 in the catheter has a single channel used for both filling and removal of effluent. One of skill in the art will understand that separate effluent and infusion lines can be used. The system 100 can be embodied an integrated cycler wherein the peritoneal dialysis cycler 116 includes the peritoneal dialysate effluent line 128, the peritoneal dialysate generation flow path 104, and the at least one sensor 106-106*h* forming the system 100 for sampling peritoneal dialysate removed from a peritoneal cavity 10. Alternatively, the peritoneal dialysis cycler 116 can be nonintegrated without the peritoneal dialysate generation flow path 104. Peritoneal dialysate can be prepared off-line and provided to the cycler 116. The computing device 120 can be a part of the peritoneal dialysis cycler 116, whether integrated or nonintegrated, or can be separate device in communication with the sensors.

The peritoneal dialysate effluent line 128 can be fluidly connected to a waste reservoir (not shown) to collect effluent. Optionally, a sampling flow path 130 can be in fluid communication with the peritoneal dialysate effluent line 102 for analysis of the fluid A valve (not shown) in the cycler can divert fluid from the effluent line 128 to the sampling flow path 130. The system 100 can divert a sample of effluent flowing through the peritoneal dialysate effluent line 102 to allow determination of fluid characteristics outside of the cycler 116. The sample can be diverted continuously or at specific intervals and in predetermined amounts. A valve (not shown) can be included to selectively divert peritoneal dialysate from the peritoneal dialysate effluent line 102 into the sampling flow path 130. A pump (not shown) can provide an additional driving force for moving peritoneal dialysate through the sampling flow path 130. A similar analysis can be conducted on the generated peritoneal dialysate by diverting a volume of generated peritoneal dialysate into the sampling flow path 130. Analysis of the generated peritoneal dialysate can serve as a quality check on the newly generated peritoneal dialysate, as well as calibration of the sensors by comparing sensed values to known values of the dialysate. Analysis of the newly generated dialysate can also be used by the system for self-learning or machine learning to adjust the dialysate composition to a precision beyond the capabilities of known systems. Analysis of the generated peritoneal dialysate can also be used as a safety system to ensure the concentration of solutes in the peritoneal dialysate is within a predetermined threshold of the expected values.

Alternatively or additionally, the system 100 can include a sampling port 134. The sampling port 134 can be fluidly connected to the peritoneal dialysate effluent line 102. The sampling port 134 can alternatively be fluidly connected to the sampling flow path 130. The sampling port 134 can be covered by a pierceable septum. A user can insert a needle or syringe through the pierceable septum to draw out a portion of the peritoneal dialysate in the effluent line 102 or sampling flow path 130. The pierceable septum can re-seal after removal of the needle or syringe to avoid contamination of the peritoneal dialysate.

When used with an integrated cycler, the peritoneal dialysate generation flow path 104 can include a water source 108, one or more water purification modules 110, a concentrate source 112, a sterilization module 114, and the peritoneal dialysis cycler 116. The concentrate source 112 can contain one or more solutes. The water source 108, water purification module 110, concentrate source 112, sterilization module 114, and peritoneal dialysis cycler 116 can be fluidly connectable to the peritoneal dialysate generation flow path 104. The peritoneal dialysate generation flow path 104 can be fluidly connected to the combined infusion and effluent line 128 to infuse peritoneal dialysate into the peritoneal cavity 10. One of skill in the art will understand that with a single concentrate source, solutes can be altered in the dialysate without changing the relative proportions of each solute. With multiple concentrate sources, each individual solute can be adjusted independently of all other solutes. The concentration of the ionic compounds in the ion concentrate source can also be lower than the concentration generally used in dialysis for generation of low concentration dialysate. Any number of concentrate sources and concentrate pumps can be used. A separate osmotic agent source and ion concentrate source can be used to adjust the osmotic agent concentration and other solute concentrations independently. Any solute usable in peritoneal dialysis can be included in the concentrate sources. The water source 108 can be a non-purified water source, such as tap water, wherein the water from the water source 108 can be purified by the system. A non-purified water source can provide water without additional purification, such as tap water from a municipal water source, water that has undergone some level of purification, but does not meet the definition of "purified water" provided, such as bottled water or filtered water. The water source can contain water meeting the WHO drinkable water standards provided in Guidelines for Drinking Water Quality, World Health Organization, Geneva, Switzerland, 4th edition, 2011. Alternatively, the water source 108 can be a source of purified water, meaning water that meets the applicable standards for use in peritoneal dialysis without additional purification. The system pumps water from the water source to a water purification module to remove chemical contaminants in the fluid in preparation of the dialysate. The water purification module can be a sorbent cartridge containing anion and cation exchange resins and/or activated carbon. The system can pump the fluid to a sterilization module 114 for sterilizing the peritoneal dialysate prior to infusion into the patient. The sterilization module 114 can include one or more of a first ultrafilter, a second ultrafilter, and a UV light source, or any combination thereof. The sterilization module can be any component or set of components capable of sterilizing the peritoneal dialysate.

The concentrate sources 112 can contain one or more solutes for generating the peritoneal dialysate from purified water. The concentrates in the concentrate source 112 are utilized to generate a peritoneal dialysis fluid that matches a dialysis prescription. A concentrate pump (not shown) in communication with the processor or computing unit controls the movement of fluid from the concentrate sources 112 into the peritoneal dialysate generation flow path 104. One of skill in the art will understand that any number of concentrate sources can be used, each containing concentrates of one or more substances. For example, the concentrate sources 112 can include any number of concentrates combined or in separate concentrate sources. One or more osmotic agent sources can be included in addition to a single ion concentrate source. Alternatively, multiple ion concentrate sources can be used with each ion concentrate in a separate concentrate source. Any combination of concentrates in any number of concentrate sources can be used with the invention. The concentrate sources can infuse each particular concentrate to provide an infused ion concentration that is lower than a prescribed amount for a particular patient. One desired outcome can be to provide a concentration for a particular ion that is lower than a patient's pre-dialysis ion concentration. Additionally, if multiple ion sources are to be delivered by a concentrate source, the present system can selectively dilute a desired ion while maintaining concentration levels for other ions. Hence, the present invention can avoid adjusting down every ion insofar as an added diluent may adversely affect concentrations of ions already in a normal range.

One or more fluid characteristics in the peritoneal dialysate removed from the patient can be determined by one or more sensors 106-106h. The sensors 106-106h can be fluidly connected to one or more of the peritoneal dialysate effluent line 128, the sampling flow path 130, the sampling reservoir 132, and the peritoneal dialysate generation flow path 104. For use with non-invasive sensors, the sensors 106 can be positioned in the effluent line 128 and the sampling flow path 130 can be optional. The sample can be tested while in the peritoneal dialysate effluent line 128, the peritoneal dialysate generation flow path 104, or in the sampling flow path 130. Additionally or alternatively, a sample can be diverted away from the peritoneal dialysate effluent line 102 and then tested. For example, the sample can be diverted into the sampling flow path 130 fluidly connected to the peritoneal dialysate effluent line 102. The sample can be diverted through the sampling flow path 130 into a detachable sampling reservoir 132 fluidly connected to the sampling flow path 130 for removal of the dialysate from the cycler 116 and off-line testing. Certain fluid characteristics, such as color or clarity of the dialysate can require specialized equipment not included in the effluent line 128, or the sampling flow path 130. The detachable sampling reservoir 132 allows a portion of the peritoneal dialysate to be removed for determining any fluid characteristics with sensors not present in the effluent line 128 or sampling flow path 130. The sample can be tested while in the sampling flow path 130 and/or the detachable sampling reservoir 132. Alternatively, the sample can be diverted directly to standalone system, such as a blood analyzer for analysis. Blood analyzers can determine several fluid characteristics, which can be included in the system. One non-limiting example of a standalone analyzer is the Stat Profile® Critical Care Xpress analyzer by Nova Biomedical, however any analyzer can be used. The standalone analyzer can be in communication with the processor or computing unit of the system to provide the system with the results of the analysis. Specialized tubing with a T-junction or a valve can be used to divert a volume of fluid into the sampling flow path or to a standalone analyzer. In an embodiment, one or more sensors 106-106h can be external to the peritoneal dialysis cycler 116 and the sample can be tested external to the peritoneal dialysis cycler 116 in the sampling flow path 130. The system an also include duplication of analysis with duplicated sensors in multiple locations. For example, the same type of sensor can be included in both the effluent line 128 and in the sampling flow path 130. Alternatively, a separate analyzer can be included for duplication of analysis. Duplication of the analysis allows calibration of the sensors and acts as a safety check to ensure the sensors are properly functioning. The duplicated sensors can be attached to the cycler 116 or in a standalone system.

The one or more sensors can be separate sensors or one or more combined sensors. The one or more sensors 106-106h can be in fluid communication with and positioned in or along one or more of the peritoneal dialysate effluent line 128, the sampling flow path 130, the detachable sampling reservoir 132, and the peritoneal dialysate generation flow path 104.

Multiple instances of the one or more sensors 106-106h are shown in FIG. 1. For example, a flow sensor 106a can measure a volume of peritoneal dialysate removed from a patient. A solute concentration sensor 106b can measure a solute concentration of the peritoneal dialysate removed from the patient. The solute concentration sensor 106b can include a conductivity sensor or an ion selective electrode for determining the concentration of the ionic components of peritoneal dialysate removed from the patient. A refractive index sensor 106c can measure glucose or other osmotic agent concentration in the peritoneal dialysate removed from the patient. A conductivity sensor 106d can measure conductivity of the peritoneal dialysate removed from the patient. A pressure sensor 106e can measure a pressure of peritoneal dialysate removed from the patient, and/or a pressure to infuse peritoneal dialysate into the patient, when included in infusion line 104. A temperature sensor 106f can measure a temperature of peritoneal dialysate removed from the patient. A pH sensor 106g can measure a pH level of peritoneal dialysate removed from the patient. An ion selective electrode 106h can measure the concentration of one or more specific solutes in the peritoneal dialysate removed from the patient. Table 1 provides non-limiting examples of sensors and methods that can determine solute concentrations for a variety of solutes. Any one or more of the reagents in Table 1 can be added to the peritoneal dialysate to determine a fluid characteristic. One of skill in the art will understand that alternative or additional methods can be used, and any sensor or method known in the art can be incorporated.

TABLE 1

| Analyte | Test Name | Key Reagents | Detection |
|---|---|---|---|
| Total protein | A280 | None | UV/Visible spectrophotometer @ 280 nm |
| Total protein | Coomassie (Bradford Assay) | Coomassie Brilliant Blue G-250 | UV/Visible spectrophotometer @ 595 nm |
| Total protein | Bicinchoninic Acid (BCA, Smith Assay) Lowry Assay | Bicinchoninic acid Copper (II) sulfate | UV/Visible spectrophotometer @ 562 nm |
| Total protein | Pierce assay | Proprietary Dye compounds | UV/Visible spectrophotometer @ 660 nm |
| Calcium | | 0-cresolphthalein | UV/Visible spectrophotometer @ 575 nm |

TABLE 1-continued

| Analyte | Test Name | Key Reagents | Detection |
| --- | --- | --- | --- |
| Calcium | | None | Ion selective electrode |
| Potassium | | None | Ion selective electrode |
| Magnesium | | None | Ion selective electrode |
| Glucose | | Glucose oxidase + platinum electrode that reduces hydrogen peroxide to produce an electric signal | Potentiometric |
| Glucose | | Glucose oxidase + peroxide reactive dye (several available) | UV/Visible spectrophotometer @ dye specific wavelength |

Referring to the tests listed in Table 1, UV/Vis spectrophotometry is an absorption spectroscopy or reflectance spectroscopy technique that operates in the visible or ultraviolet spectral range. A UV/Vis spectrophotometer exposes a chemical sample to light at predetermined wavelength and measures either the absorption or reflection spectra that is produced. The absorbance of the solution is proportional to the concentration of the absorbing species and the path length, so the concentration of the unknown sample can be quantified using a calibration curve developed using a series of samples of known concentration. Determination of protein concentration by measuring absorbance at 280 nm (A280) is based on the absorbance of UV light by the aromatic amino acids tryptophan and tyrosine, and by cystine, disulfide bonded cysteine residues, in protein solutions. Absorption correlates with concentration, which can be quantified using a calibration curve developed with standards of known concentration. The Bradford (Coomassie) assay reacts Coomassie blue dye with protein in an acidic/methanol solution. The protein-dye complex has a blue color, whereas the unbound dye has a brown color. The amount of protein in the solution can be quantified by measuring the intensity of the blue color at 595 nm and comparing to a calibration curve developed with standards of known concentration. The BCA (Smith) Assay primarily relies on two reactions. First, the peptide bonds in protein reduce $Cu^{2+}$ ions from the copper(II) sulfate to $Cu^+$ (a temperature dependent reaction). The amount of $Cu^{2+}$ reduced is proportional to the amount of protein present in the solution. Next, two molecules of bicinchoninic acid chelate with each $Cu^+$ ion, forming a purple-colored complex that strongly absorbs light at a wavelength of 562 nm. Other commercially available protein assays have been developed to provide greater specificity and/or address interferences that can decrease utility of the assays described above. Many of the assays use proprietary dye molecules, but all use the general procedure of preparing a protein-dye complex that results in a color change that can be detected spectrophotometrically. Calcium ions (Ca2+) react with o-cresolphthalein complexone in an alkaline solution to form an intense violet colored complex which maximally absorbs at 577 nm. 2,3 8-Hydroxyquinoline can be added to remove interference by magnesium and iron. In the method the absorbance of the Ca-oCPC complex is measured bichromatically at 570/660 nm. The resulting increase in absorbance of the reaction mixture is directly proportional to the calcium concentration in the sample. An ion-selective electrode (ISE) is a transducer (or sensor) that converts the activity of a specific ion dissolved in a solution into an electrical potential. The voltage is theoretically dependent on the logarithm of the ionic activity, according to the Nernst equation. The ISE has a coating over the electrodes that allow specific ions to interact with the electrodes, but reject other ions. Many types of ISE are commercially available with different specificity and durability as needed for a specific application. ISE electrodes are available for calcium, magnesium, potassium and other ions of interest in PD fluid. Glucose can be quantified using a sensor that utilizes glucose oxidase. Glucose oxidase is an enzyme that oxidizes glucose to D-glucono-1,5 lactone+hydrogen peroxide. The hydrogen peroxide that is produced can be reduced on a platinum electrode to produce an electrical signal proportional to concentration. Alternatively, the peroxide can be complexed with a reactive dye, such as Amplex® Red reagent (10-acetyl-3,7-dihydroxyphenoxazine) to produce a colored complex that can be quantified using a UV/Vis spectrophotometer. Other peroxide reactive dyes are commercially available to measure peroxide concentration.

The computing device 120 can include the one or more processors 122, memory 124, and one or more input/output interfaces 126. One of ordinary skill in the art will recognize that the memory 124 can include long-term memory and operating memory, and/or memory serving as both long-term memory and operating memory. The memory 124 can be a machine-readable storage medium. The memory 124 can be in communication with the processor 122 and store instructions that when executed perform any of the methods of the present invention. The input/output interface(s) 126 can include an input port to receive information from the one or more sensors 106-106h, and an output interface to output data to a user, such as a notification regarding the sample. The processor 122 can be in communication with the at least one sensor 106-106h and store data received from the at least one sensor 106-106h in the memory 124. As with all features of the present application, intervening components, such as the input/output interface 126, can be present between the processor 122 and the sensors 106-106h. The computing device 120 can be a stand-alone device independent of the peritoneal dialysis cycler 116, or can be a part of the peritoneal dialysis cycler 116. The computing device 120 can be a remote device in network communication with the sensor(s) 106-106h, such as via the Internet.

Figure 2:
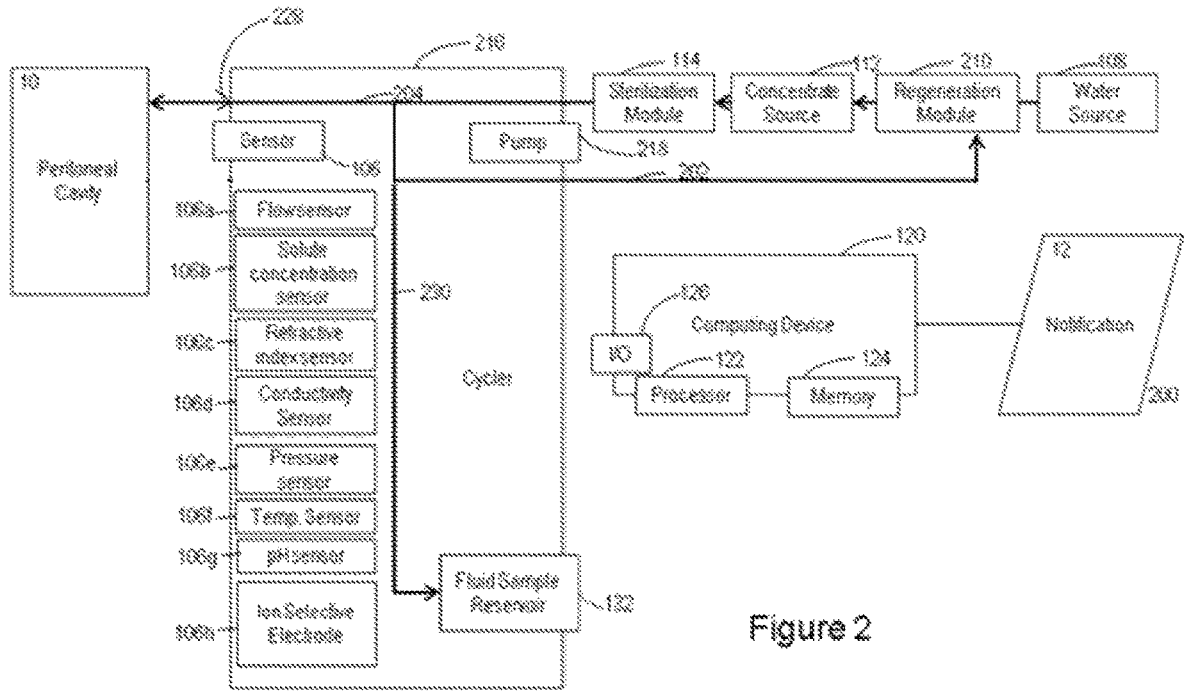
FIG. 2 is a schematic of a regenerative peritoneal dialysis system for sensing fluid characteristics of the peritoneal dialysate.

FIG. 2 shows an alternative system 200 for sampling peritoneal dialysate to determine one or more fluid characteristics of the dialysate removed from the patient. A difference between system 200 and system 100 is the provision of a peritoneal dialysate regeneration module 210. A discussion of some features similar to the features of system 100 is omitted in the interest of brevity.

The peritoneal dialysis cycler 216 can include a pump 218, a combined infusion and effluent line 228, referred to herein as an effluent line, and a dialysate regeneration line 202. The effluent line 228 can be fluidly connected to the peritoneal dialysate generation flow path 204 downstream of the sterilization module 114. The peritoneal dialysate regeneration line 202 can be fluidly connected to the peritoneal dialysate generation flow path 204 upstream of the peritoneal dialysate regeneration module 210. The peritoneal dialysate regeneration module 210 can be positioned downstream of the optional sampling flow path 230.

Certain fluid characteristics require additional reagents or dyes for determination. In one non-limiting example, determination of glucose concentration requires that glucose react with glucose oxidase to produce hydrogen peroxide. The hydrogen peroxide formed through the reaction together with 4 amino-antipyrene (4-AAP) and phenol in the presence of peroxidase yield a red quinoeimine dye that can be measured spectrophotometrically at 505 nm. Alternatively, the hydrogen peroxide can be reacted with an appropriate electrode sensor that produces electric current in proportion to glucose concentration. Similarly, the protein content in peritoneal dialysate effluent can be detected by any suitable protein bioassay. In one non-limiting example, Coomassie Brilliant Blue G-250 dye is reacted with protein to form a colored complex that can be detected spectrophotometrically. The color intensity correlates with protein concentration. One of skill in the art will understand that alternative reagents can be used to determine the same or different fluid characteristics. Many of the reagents cannot be passed back to the patient when the peritoneal dialysate is regenerated and reused. The sampling flow path 230 allows necessary reagents to be added to the dialysate removed from the patient in a diverted flow path, ensuring that the reagents are not passed back into the dialysate generation flow path 204 and to the patient. Sensors that do not require the addition of reagents can alternatively be present in the effluent line 128, and the sampling flow path 130 is optional. A detachable sampling reservoir can allow a portion of the peritoneal dialysate removed from the patient to be analyzed off-line.

The system 200 can include a peritoneal dialysate effluent line 228, a peritoneal dialysate generation flow path 204, at least one sensor 106-106$h$, a peritoneal dialysis cycler 216, and a computing device 120 as shown in FIG. 1.

Figure 3:
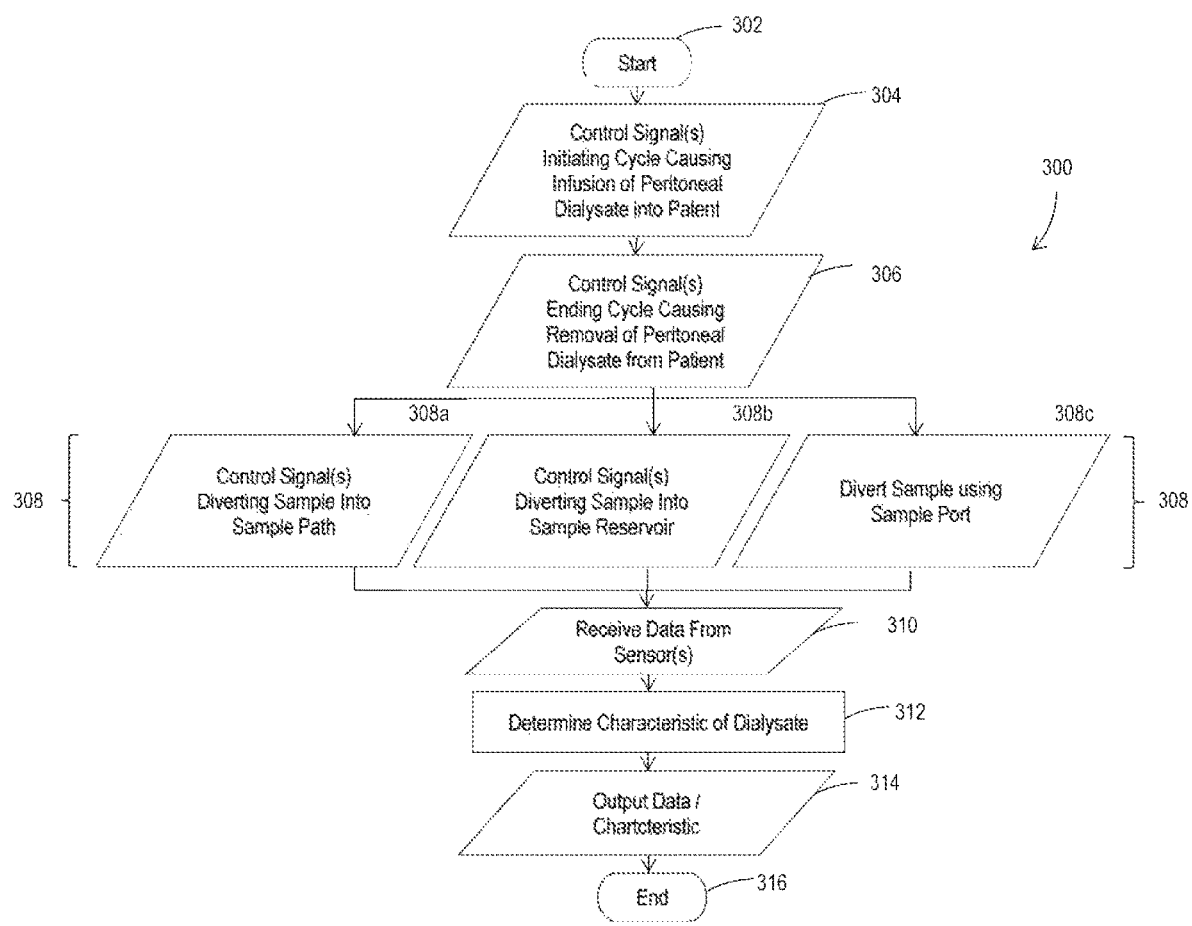
FIG. 3 is a flow chart illustrating a method of determining fluid characteristics in a sample of peritoneal dialysate.

The operation of the systems 100, 200 of FIGS. 1 and 2 is shown in FIG. 3, which is a schematic representation of an exemplary computerized method 300 for sampling peritoneal dialysate removed from a peritoneal cavity 10 of a patient. In operation 302, the method 300 can start. A peritoneal dialysis session can be initiating or already underway in operation 302.

In operation 304, a control signal(s) initiating a cycle of the peritoneal dialysis session can be issued by the processor 122 of the system 100, 200 controlling components of peritoneal dialysate generation flow path 104, 204. Peritoneal dialysate can be infused into the peritoneal cavity 10 of a patient through the effluent line 128, 228. The method can proceed to operation 306.

In operation 306, a control signal(s) ending the cycle of the peritoneal dialysis session can be issued by the processor 122 of the system 100, 200. The control signal can cause the peritoneal dialysis cycler 116, 216 to initiate a drain portion of the cycle. Peritoneal dialysate can be removed from the peritoneal cavity of the patient 10 through the peritoneal dialysate effluent line 128, 228. The method can proceed to operation 308.

In operation 308, a control signal(s) diverting a sample of the peritoneal dialysate flowing through the peritoneal dialysate effluent line 128, 228 can be issued by the processor 122. Multiple instances of operation 308 are depicted in FIG. 3. For example, in operation 308$a$, the control signal(s) can cause the sample to be removed from the peritoneal dialysate flowing through the peritoneal dialysate effluent line 128, 228 and into the sampling flow path 130, 230. In operation 308$b$, the control signal(s) can cause the sample to be removed from the peritoneal dialysate flowing through the peritoneal dialysate effluent line 128, 228 and into the detachable sampling reservoir 132. In any embodiment, the sample can be pumped from the effluent line 128, 228, through a valve into the sampling flow path 130 and optionally to the detachable sampling reservoir 132. Alternatively, the sample can be diverted from the peritoneal dialysate effluent line 128, 228 and directly into the detachable sampling reservoir 132 or a standalone analyzer. In operation 308$c$, the peritoneal dialysate can be removed from the effluent line 128, 228 through a sampling port. For example, a syringe needle can be mechanically or manually inserted through the pierceable septum and a portion of the peritoneal dialysate can be removed for off-line analysis. Alternatively, one or more of the sensors can be positioned in the effluent line 128, 228, and the system need not divert a portion of the effluent. The method 300 can proceed to operation 310.

In operation 310, data can be received by the processor 122 from the sensors 106-106$h$ regarding the sample. For example, the one or more sensors in fluid communication with the sampling flow path 130 can receive data representing a characteristic of the peritoneal dialysate. Alternatively, one or more sensors in the peritoneal dialysate effluent line 128, 228, the peritoneal dialysate generation flow path 104, 204, or a standalone analyzer, can receive data representing a characteristic of the peritoneal dialysate. Additionally or alternatively, the data received in operation 310 can be analyzed by the processor 122 to determine the characteristic of the peritoneal dialysate in operation 312. The data received from the sensors in operation 310 can be stored in a machine-readable storage medium. The method 300 can proceed to operation 314, and the data received from the sensors can be transmitted to a user. As another example, the one or more sensors in fluid communication with the detachable fluid reservoir 132 can receive data representing a characteristic of the peritoneal dialysate in the peritoneal dialysate effluent line 128, 228. As yet another example, one or more sensors 106-106$h$ can output data from the sample after the peritoneal dialysate is removed using the sampling port 134. The step of determining a characteristic of the peritoneal dialysate in operation 312 can include determining the characteristic of the peritoneal dialysate after the peritoneal dialysate is removed using the sampling port 134.

One of ordinary skill in the art will recognize that multiple fluid characteristics can be sampled by sensors 106-106$h$ of systems 100, 200 of FIGS. 1 and 2. Table 2 contains non-limiting examples of sensors 106-106$h$ and corresponding sampled characteristics of the peritoneal dialysate.

TABLE 2

| Sensor | Fluid Characteristic |
| --- | --- |
| Flow sensor | Volume of fluid |
| Refractive index sensor | Osmotic agent concentration in fluid |
| Conductivity sensor | Conductivity of fluid |
| Pressure sensor | Pressure to deliver/remove fluid |
| Temperature sensor | Temperature of fluid |
| pH sensor | pH of fluid |
| Ion selective electrode | Concentration of specific ions in fluid |

Fluid characteristics of both the peritoneal dialysate in the infusion line being infused into the patient, and the peritoneal dialysate in the effluent line can be determined. Determining the fluid characteristic in both the infusion line and the effluent line allows for determinations of changes to the peritoneal dialysate while inside the peritoneal cavity of the patient during a dwell period. For example, the pH of the peritoneal dialysate infused into the patient and the pH of the peritoneal dialysate removed from the patient allows a determination of the change in pH during the dwell period. A drop in dialysate pH during the dwell period can indicate an infection in the patient, or poor membrane transfer efficiency. Flow sensors in both the infusion line and the effluent line can be used to determine the volume of peritoneal dialysate infused into the patient and the volume of peritoneal dialysate removed from the patient. The difference between the volume of peritoneal dialysate infused into the patient and removed from the patient provides the net fluid removal, or ultrafiltration, from the patient.

The system can divert peritoneal dialysate into the effluent line at multiple times. A portion of the peritoneal dialysate in the peritoneal cavity of the patient can be removed at a first time and a second time, allowing the changes in a fluid characteristic to be determined. A decrease in the pH of the dialysate over time could indicate infection or poor membrane transfer efficiency. Membrane transfer efficiency can also be calculated by measuring changes in solute concentration of the dialysate at multiple times during the dwell period. Concentrations of solutes measured at multiple times during the dwell period can also be used to determine the optimal time to end a peritoneal dialysis cycle. For example, a plateau in the concentration of one or more solutes, including an osmotic agent concentration, could indicate that equilibrium between the patient and the dialysate has been achieved, and a new cycle started.

One skilled in the art will understand that various combinations and/or modifications and variations can be made in the systems and methods depending upon the specific needs for operation. Features illustrated or described as being part of an aspect of the invention can be used in the aspect of the invention, either alone or in combination.

We claim:

1. A peritoneal dialysis cycler, comprising:
    a combined infusion and effluent line for delivering and receiving a peritoneal dialysate to and from a peritoneal cavity;
    at least one pump positioned in the combined infusion and effluent line;
    at least one valve fluidly connecting the combined infusion and effluent line to a sampling flow path; the sampling flow path fluidly connected to at least one sensor, wherein the at least one sensor is selected from the group consisting of: an ion selective electrode, a pH sensor, a refractive index sensor, and a conductivity sensor; and
    a processor in communication with the at least one sensor; the processor programmed to determine a concentration of at least one solute in a peritoneal dialysate removed from a patient based on data from the at least one sensor and to determine an end time for a peritoneal dialysis cycle based on the concentration of the at least one solute.

2. The peritoneal dialysis cycler of claim 1, further comprising a detachable sampling reservoir fluidly connected to the sampling flow path.

3. The peritoneal dialysis cycler of claim 1, further comprising a peritoneal dialysate generation flow path fluidly connected to the combined infusion and effluent line; the peritoneal dialysate generation flow path having:
    a water source;
    a water purification module;
    at least one concentrate source fluidly connected to the peritoneal dialysate generation flow path; and
    at least one sensor positioned in the peritoneal dialysate generation flow path or combined infusion and effluent line.

4. The peritoneal dialysis cycler of claim 3, further comprising a dialysate regeneration module; the dialysate regeneration module fluidly connected to the combined infusion and effluent line and the peritoneal dialysate generation flow path.

5. The peritoneal dialysis cycler of claim 4, wherein the dialysate regeneration module is positioned downstream of the sampling flow path.

6. The peritoneal dialysis cycler of claim 1, the processor receiving data from the at least one sensor and storing the data in a machine-readable storage medium.

7. The peritoneal dialysis cycler of claim 6, the processor comprising an input/output interface, the input/output interface transmitting data from the at least one sensor to a user.

8. The peritoneal dialysis cycler of claim 1, further comprising a sampling port fluidly connected to the sampling flow path.

9. The peritoneal dialysis cycler of claim 8, wherein the sampling port is covered by a pierceable septum.

10. The peritoneal dialysis cycler of claim 1, wherein the combined infusion and effluent line comprises separate flow paths.

11. The system of claim 1, the sampling flow path fluidly connected to at least a second sensor selected from the group consisting of a flow sensor, a pressure sensor, and a temperature sensor.

12. A method, comprising the steps of:
    infusing peritoneal dialysate into a patient through a combined infusion and effluent line;
    removing peritoneal dialysate from the patient through the combined infusion and effluent line;
    operating at least one valve to direct at least a portion of the fluid in the combined infusion and effluent line into a sampling flow path;
    determining a concentration of at least one solute in the peritoneal dialysate in the sampling flow path with at least one sensor; the at least one sensor selected from the group consisting of: an ion selective electrode, a pH sensor, a refractive index sensor, and a conductivity sensor; and
    determining an end time for a peritoneal dialysis cycle based on the concentration of the at least one solute.

13. The method of claim 12, further comprising the step of pumping the peritoneal dialysate from the sampling flow path to a sampling reservoir; wherein the step of determining the concentration of the at least one solute in the peritoneal dialysate of the peritoneal dialysate in the sampling flow path comprises determining the concentration of the at least one solute in the peritoneal dialysate in the peritoneal dialysate in the sampling reservoir.

14. The method of claim 13, further comprising the step of adding one or more reagents to the peritoneal dialysate in the sampling reservoir prior to determining the concentration of the at least one solute in the peritoneal dialysate.

15. The method of claim 12, further comprising the step of removing a portion of fluid from the sampling flow path through a sampling port, wherein the step of determining the concentration of the at least one solute in the peritoneal dialysate comprises determining the concentration of the at least one solute in the removed fluid.

16. The method of claim 12, further comprising the step of determining at least one fluid characteristic in the peritoneal dialysate in the combined infusion and effluent line.

17. The method of claim 16, wherein at least one fluid characteristic is determined in the combined infusion and effluent line.

18. The method of claim 17, wherein the at least one fluid characteristic is selected from the group of a pH of the fluid, and a volume of the fluid.

19. The method of claim 12, comprising the steps of directing a portion of the peritoneal dialysate from the patient from the combined infusion and effluent line to the sampling flow path at a first time during a peritoneal dialysis cycle; directing a portion of the peritoneal dialysate from the patient from the combined infusion and effluent line to the sampling flow path at a second time; and determining the concentration of the at least one solute in the peritoneal dialysate at the first time and the second time.

20. The method of claim 12, further comprising the step of communicating the concentration of the at least one solute in the peritoneal dialysate to a machine-readable storage medium in a processor.

21. The method of claim 12, wherein the combined infusion and effluent lines are separate lines.

* * * * *